United States Patent
Thigpen et al.

(10) Patent No.: US 12,171,569 B2
(45) Date of Patent: Dec. 24, 2024

(54) MISCARRIAGE IDENTIFICATION AND PREDICTION FROM WEARABLE-BASED PHYSIOLOGICAL DATA

(71) Applicant: Oura Health Oy, Oulu (FI)

(72) Inventors: Nina Nicole Thigpen, Jersey City, NJ (US); Neta A. Gotlieb, Albany, CA (US); Gerald Pho, Somerville, MA (US); Kirstin Elizabeth Aschbacher, San Francisco, CA (US)

(73) Assignee: Oura Health Oy, Oulu (FI)

( * ) Notice: Subject to any disclaimer, the term of this patent is extended or adjusted under 35 U.S.C. 154(b) by 246 days.

(21) Appl. No.: 17/710,045

(22) Filed: Mar. 31, 2022

(65) Prior Publication Data
US 2022/0313147 A1 Oct. 6, 2022

Related U.S. Application Data

(60) Provisional application No. 63/169,314, filed on Apr. 1, 2021.

(51) Int. Cl.
*A61B 5/00* (2006.01)
*A61B 5/01* (2006.01)
(Continued)

(52) U.S. Cl.
CPC .......... *A61B 5/4343* (2013.01); *A61B 5/0002* (2013.01); *A61B 5/01* (2013.01);
(Continued)

(58) Field of Classification Search
CPC ..... A61B 5/4343; A61B 5/01; A61B 5/02055; A61B 5/02405; A61B 5/02416;
(Continued)

(56) References Cited

U.S. PATENT DOCUMENTS

2016/0058429 A1* 3/2016 Shinar ................ A61B 5/4809
                                                                600/551
2017/0340261 A1* 11/2017 Torres ................ A61B 5/1101
(Continued)

FOREIGN PATENT DOCUMENTS

| GB | 2533774 A | * 7/2016 | ......... A61B 10/0012 |
| JP | 2012125349 A |   7/2012 | |
| KR | 20160040670 A | * 4/2016 | |

OTHER PUBLICATIONS

Alihosseini E, Najar S, Haghighizadeh M H. The Relationship Between Sleep Disorders During Pregnancy and Miscarriage. Jundishapur J Chronic Dis Care. 2017;6(2):e41340. https://doi.org/10.5812/jjcdc.41340. (Year: 2017).*
(Continued)

*Primary Examiner* — Michael J Lau
(74) *Attorney, Agent, or Firm* — Holland & Hart LLP

(57) ABSTRACT

Methods, systems, and devices for miscarriage identification are described. A system may be configured to receive physiological data associated with a user that is pregnant and collected over a plurality of days, where the physiological data includes at least temperature data. Additionally, the system may be configured to determine a time series of temperature values. The system may then identify that the temperature values are lower than a pregnancy baseline of temperature values for the user and detect an indication of an early pregnancy loss of the user. The system may generate a message for display on a graphical user interface on a user device that indicates the indication of the early pregnancy loss.

20 Claims, 12 Drawing Sheets

(51) Int. Cl.
| | |
|---|---|
| *A61B 5/0205* | (2006.01) |
| *A61B 5/024* | (2006.01) |
| *A61B 5/08* | (2006.01) |
| *A61B 5/11* | (2006.01) |
| *A61B 5/1455* | (2006.01) |
| *A61B 10/00* | (2006.01) |
| *G08B 21/04* | (2006.01) |
| *G16H 40/63* | (2018.01) |
| *G16H 40/67* | (2018.01) |
| *G16H 50/20* | (2018.01) |
| *G16H 50/30* | (2018.01) |

(52) U.S. Cl.
CPC ...... *A61B 5/02055* (2013.01); *A61B 5/02405* (2013.01); *A61B 5/02416* (2013.01); *A61B 5/02438* (2013.01); *A61B 5/0816* (2013.01); *A61B 5/1118* (2013.01); *A61B 5/14551* (2013.01); *A61B 5/4806* (2013.01); *A61B 5/4809* (2013.01); *A61B 5/4812* (2013.01); *A61B 5/486* (2013.01); *A61B 5/6801* (2013.01); *A61B 5/6802* (2013.01); *A61B 5/6826* (2013.01); *A61B 5/7264* (2013.01); *A61B 5/7267* (2013.01); *A61B 5/7275* (2013.01); *A61B 5/7282* (2013.01); *A61B 5/742* (2013.01); *A61B 5/7435* (2013.01); *A61B 5/7475* (2013.01); *A61B 10/0012* (2013.01); *G08B 21/0453* (2013.01); *G16H 40/63* (2018.01); *G16H 40/67* (2018.01); *G16H 50/20* (2018.01); *G16H 50/30* (2018.01); *A61B 2010/0019* (2013.01); *A61B 2010/0029* (2013.01)

(58) Field of Classification Search
CPC . A61B 5/02438; A61B 5/0816; A61B 5/1118; A61B 5/14551; A61B 5/4806; A61B 5/4809; A61B 5/4812; A61B 5/486; A61B 5/6801; A61B 5/6802; A61B 5/6826; A61B 5/7264; A61B 5/7267; A61B 5/7275; A61B 5/7282; A61B 5/742; A61B 5/7435; A61B 5/7475; A61B 2010/0019; A61B 2010/0029; G16H 40/67; G16H 50/30; G16H 50/20; G16H 40/63; G08B 21/0453

USPC ........................................................ 600/301
See application file for complete search history.

(56) References Cited

U.S. PATENT DOCUMENTS

| | | | |
|---|---|---|---|
| 2019/0110692 A1* | 4/2019 | Pardey | A61B 10/0012 |
| 2020/0128670 A1* | 4/2020 | Chong Rodriguez | A61B 5/329 |
| 2020/0222032 A1* | 7/2020 | Stein | A61B 10/0012 |
| 2021/0007658 A1* | 1/2021 | Kinnunen | A61B 5/742 |

OTHER PUBLICATIONS

International Search Report and Written Opinion—PCT/US2022022905—ISA/EPO—Jul. 5, 2022.

"Big Data and IoT for real-time miscarriage prediction A clustering comparative study", Procedia Computer Science, vol. 191, Jan. 2021.

Hurst Bradley S: "Atypical Core Body Temperature Patterns and the Wider Implications for Conditions Related to Pregnancy, Intertility, and Miscarriage Risk" Fertility and Sterility, Elsevier, vol. 114, No. 3, Sep. 2020.

* cited by examiner

MISCARRIAGE IDENTIFICATION AND PREDICTION FROM WEARABLE-BASED PHYSIOLOGICAL DATA

CROSS REFERENCE

The present application for patent claims the benefit of U.S. Provisional Patent Application No. 63/169,314 by Aschbacher et al., entitled "WOMEN'S HEALTH TRACKING," filed Apr. 1, 2021, assigned to the assignee hereof, and expressly incorporated by reference herein.

FIELD OF TECHNOLOGY

The following relates to wearable devices and data processing, including miscarriage identification and prediction from wearable-based physiological data.

BACKGROUND

Some wearable devices may be configured to collect data from users associated with body temperature and heart rate. For example, some wearable devices may be configured to detect cycles associated with reproductive health. However, conventional cycle detection techniques implemented by wearable devices are deficient.

DETAILED DESCRIPTION

Figure 1:
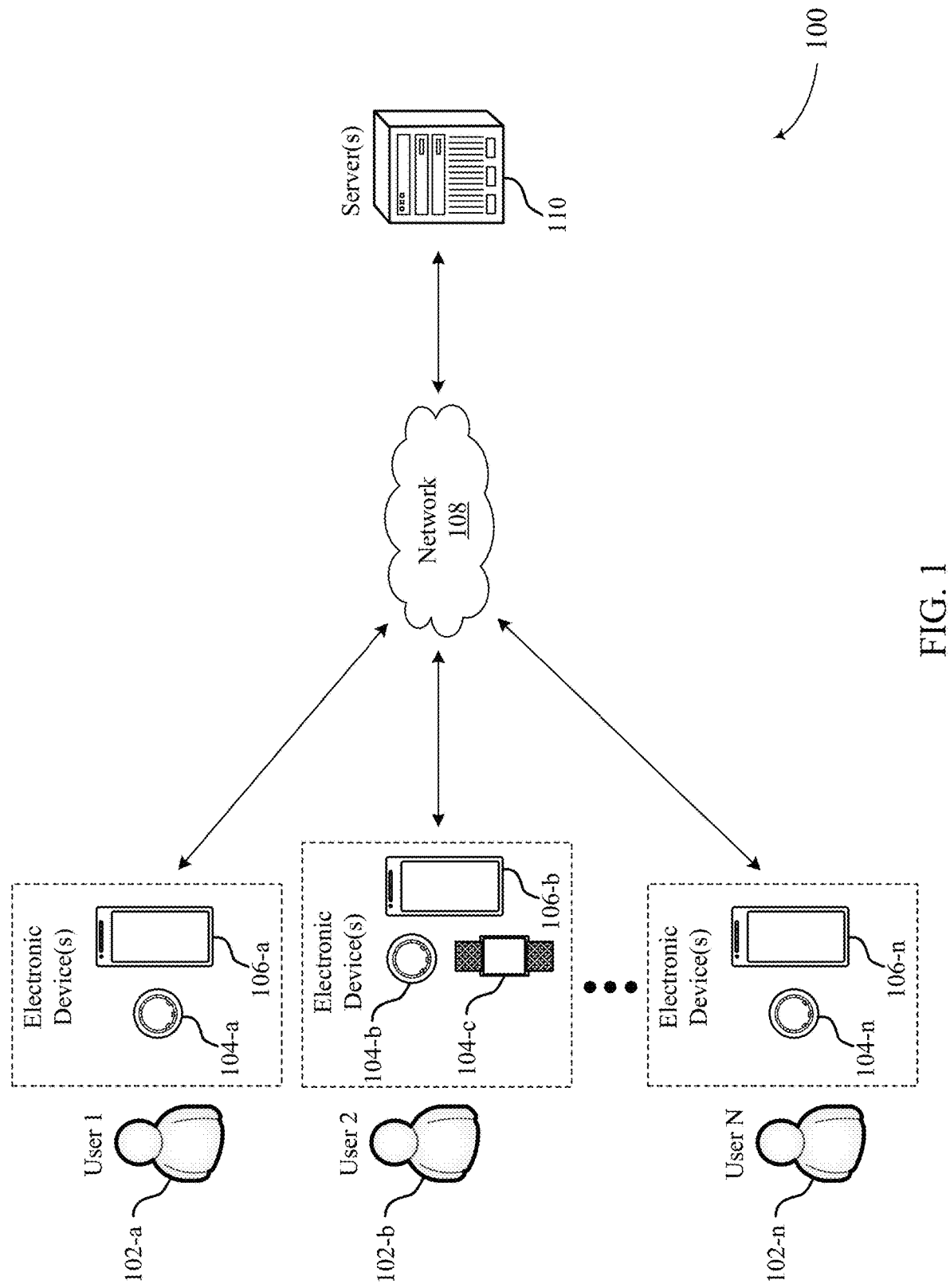
FIG. 1 illustrates an example of a system that supports miscarriage identification and prediction from wearable-based physiological data in accordance with aspects of the present disclosure.

Some wearable devices may be configured to collect physiological data from users, including temperature data, heart rate data, and the like. Acquired physiological data may be used to analyze the user's movement and other activities, such as sleeping patterns. Many users have a desire for more insight regarding their physical health, including their sleeping patterns, activity, and overall physical well-being. In particular, many users may have a desire for more insight regarding women's health, including their menstrual cycle, ovulation, fertility patterns, and pregnancy. However, typical cycle tracking or women's health devices and applications lack the ability to provide robust prediction and insight for several reasons.

First, typical cycle prediction applications require users to manually take their temperature with a device at a discrete time each day. This single temperature data point may not provide sufficient context to accurately capture or predict the true temperature variations indicative of woman's health cycle patterns and pregnancy patterns, and may be difficult to accurately capture given the sensitivity of the measuring device to user movement or exertion. Second, even for devices that are wearable or that take a user's temperature more frequently throughout the day, typical devices and applications lack the ability to collect other physiological, behavioral, or contextual inputs from the user that can be combined with the measured temperature to more comprehensively understand the complete set of physiological contributors to a women's cycle and pregnancy.

Aspects of the present disclosure are directed to techniques for identifying an indication of an early pregnancy loss. In particular, computing devices of the present disclosure may receive physiological data including temperature data, from the wearable device associated with the user and determine a time series of temperature values taken over a plurality of days. The physiological data may be associated with a user who is pregnant. For example, aspects of the present disclosure may identify one or more morphological features from a graphical representation of the time series of temperature values, such as deviations of the time series of temperature values relative to a pregnancy baseline of temperature values for the user. As such, aspects of the present disclosure detect an indication of an early pregnancy loss of the user based on identifying the morphological features (e.g., deviations). In such cases, an indication of an early pregnancy loss may be associated with temperature values that are lower than the pregnancy baseline of temperature values of the user. The indication of early pregnancy loss may be an example of detecting that the early pregnancy loss has already happened, is currently happening, and/or that the early pregnancy loss is predicted to happen in the future.

In some implementations, the system may analyze historical temperature data from a user and pregnancy baseline values of the user and identify an indication of the early pregnancy loss and may generate an indication that indicates the user's early pregnancy loss. The user may confirm whether the early pregnancy loss has already occurred as indicated by the system, and the system may incorporate this user input into a predictive function (e.g., a machine learning model for predicting a future early pregnancy loss). The system may also analyze temperature series data in real time and may predict an upcoming early pregnancy loss based on identifying one or more morphological features in the time series of the temperature data and/or based on the user's input.

For the purposes of the present disclosure, the term "early pregnancy loss" may be used to refer to a spontaneous loss of a user's pregnancy before the twentieth week of pregnancy. An early pregnancy loss (e.g., miscarriage) begins with a loss of blood, fluid, or tissue and/or pain in the belly or lower back. For example, a user may be experiencing a miscarriage when the user's body discards the fetus from the womb before the fetus is able to survive independently.

Some aspects of the present disclosure are directed to the detection of the early pregnancy loss before the user experiences symptoms and effects of the menstrual cycle early pregnancy loss. However, techniques described herein may also be used to detect the early pregnancy loss in cases where the user does not become symptomatic, or does not become aware of their symptoms. In some implementations, the computing devices may identify an indication of the early pregnancy loss using a temperature sensor. In such cases, the computing devices may estimate the retrospective dates of the early pregnancy loss without the user tagging or labeling these events.

In conventional systems, an early pregnancy loss may be detected by using a fetal doppler and/or ultrasound after the early pregnancy loss has occurred. In other cases, an early pregnancy loss may be detected based on symptoms experienced by the user (e.g., cramping, bleeding, pain, etc.). In such cases, the early pregnancy loss may be detected after occurrence and/or confirmed at an appointment with the clinician. Techniques described herein may continuously collect the physiological data from the user based on measurements taken from a wearable that continuously measures a user's surface temperature and signals extracted from blood flow such as arterial blood flow (e.g., via PPG signal). In some implementations, the computing devices may sample the user's temperature continuously throughout the day and night. Sampling at a sufficient rate (e.g., one sample per minute) throughout the night may provide sufficient temperature data for analysis described herein.

In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body or if the user were manually taking their temperature once per day. As such, data collected by the computing devices may be used to identify when the user experiences an early pregnancy loss.

Techniques described herein may notify a user, clinician, fertility specialist, care-giver, or a combination thereof of the indication of the early pregnancy loss in a variety of ways. For example, a system may generate a message for display on a graphical user interface (GUI) of a user device that indicates the indication of the early pregnancy loss. In such cases, the system may cause the GUI of a user device to display a message or other notification to notify the user, clinician, etc. of the detected early pregnancy loss, notify the user of an estimated likelihood of a future early pregnancy loss, make recommendations to the user, and the like. In some implementations, the system may make tag recommendations to a user. For example, the system may recommend early pregnancy symptom tags (e.g., cramps, back pain) to users in a personalized manner.

The system may also include graphics or text that indicate the data used to make the detection/prediction of a likely pregnancy loss. For example, the GUI may display a notification of the likelihood of an early pregnancy loss based on temperature deviations from a pregnancy baseline of the user. In some cases, the GUI may display a notification of the likelihood of an early pregnancy loss based on heart rate deviations from a normal baseline, breath rate deviations from a normal baseline, heart rate variability (HRV) from a normal baseline, or a combination thereof. Based on the early detection (e.g., before the user experiences symptoms), a user may take early steps that may help reduce the severity of upcoming symptoms associated with the early pregnancy loss or limit the risk of having an early pregnancy loss altogether.

Aspects of the disclosure are initially described in the context of systems supporting physiological data collection from users via wearable devices. Additional aspects of the disclosure are described in the context of example timing diagrams and example GUIs. Aspects of the disclosure are further illustrated by and described with reference to apparatus diagrams, system diagrams, and flowcharts that relate to miscarriage identification and prediction from wearable-based physiological data.

FIG. 1 illustrates an example of a system 100 that supports miscarriage identification and prediction from wearable-based physiological data in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, HRV, actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) that emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time during which a user 102 is asleep, and classify periods of time during which the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time during which the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for miscarriage identification and prediction based on data collected by a wearable device 104. In particular, the system 100 illustrated in FIG. 1 may support techniques for detecting the indication of the early pregnancy loss of a user 102, and causing a user device 106 corresponding to the user 102 to display the indication of the early pregnancy loss. The indication of early pregnancy loss may be an example of detecting that the early pregnancy loss has already happened, detecting that the early pregnancy loss is currently happening, and/or that the early pregnancy loss is predicted to occur in the future.

For example, as shown in FIG. 1, User 1 (user 102-*a*) may be associated with a wearable device 104-*a* (e.g., ring 104-*a*) and a user device 106-*a*. In this example, the ring 104-*a* may collect data associated with the user 102-*a*, including temperature, heart rate, HRV, respiratory rate, and the like. In some aspects, data collected by the ring 104-*a* may be used to detect the indication of the early pregnancy loss during which User 1 experiences a miscarriage. Identifying and/or predicting the early pregnancy loss may be performed by any of the components of the system 100, including the ring 104-*a*, the user device 106-*a* associated with User 1, the one or more servers 110, or any combination thereof. Upon identifying and/or predicting the early pregnancy loss, the system 100 may selectively cause the GUI of the user device 106 to display the indication of the early pregnancy loss. In such cases, the user device 106 may be associated with User 1, User 2, User N, or a combination thereof where User 2 and User N may be an example of a clinician, a caregiver, a user associated with User 1, or a combination thereof.

In some implementations, upon receiving physiological data (e.g., including temperature data), the system 100 may determine a time series of temperature values taken over a plurality of days. The system 100 may identify that the temperature values are lower than a pregnancy baseline of temperature values for the user. As described in more detail herein, a pregnancy baseline may refer to a baseline or average temperature, or usual temperature variations for the user as measured throughout pregnancy or specific phases of pregnancy, which may differ from the user's normal or non-pregnant baselines. In such cases, the system 100 may detect the indication of the early pregnancy loss of the user based on identifying that the temperature values are lower than the pregnancy baseline of temperature values for the user.

In some implementations, the system 100 may generate alerts, messages, or recommendations for User 1, User, 2, and/or User N (e.g., via the ring 104-a, user device 106-a, or both) based on the detected indication of early pregnancy loss, where the messages may provide insights regarding the detected indication of early pregnancy loss, such as a timing of the early pregnancy loss. In some cases, the messages may provide insight regarding symptoms associated with the early pregnancy loss, educational videos and/or text (e.g., content) associated with the early pregnancy loss, recommendations to improve symptoms associated with the early pregnancy loss, or a combination thereof.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
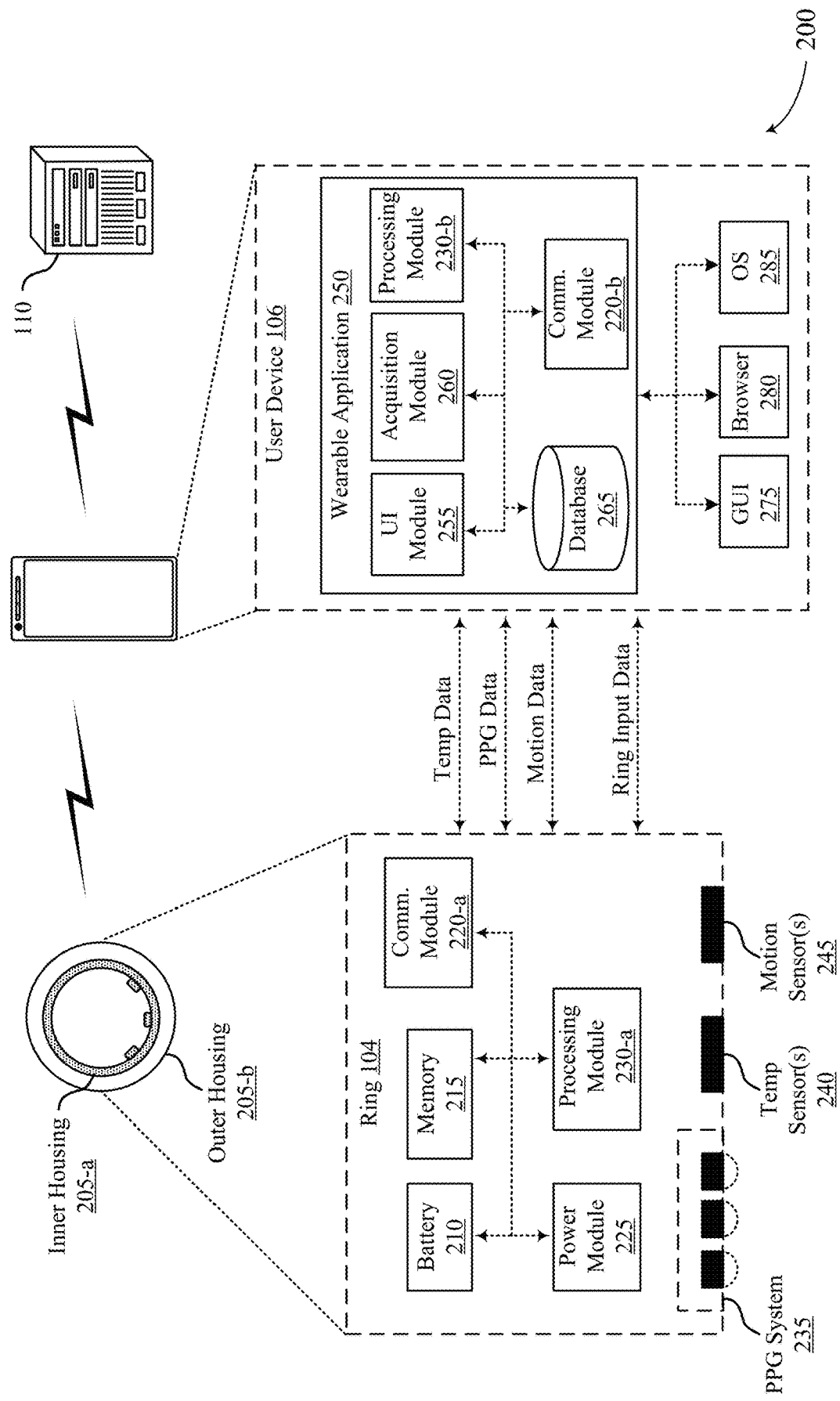
FIG. 2 illustrates an example of a system that supports miscarriage identification and prediction from wearable-based physiological data in accordance with aspects of the present disclosure.

FIG. 2 illustrates an example of a system 200 that supports miscarriage identification and prediction from wearable-based physiological data in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

System 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium, that may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or which supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-a) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-a may sample the user's temperature over time. For example, the processing module 230-a may sample the user's temperature according to a sampling rate. An example sampling rate may include one sample per second, although the processing module 230-a may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second, one sample per minute, and the like) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 in which the optical receiver(s) receive transmitted light that is reflected through the region of the user's finger. In some implementations, the PPG system 235 may be configured as a transmissive PPG system 235 in which the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time in which the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for miscarriage identification and prediction. In particular, the respective components of the system 200 may be used to detect the indication of the early pregnancy loss based on identifying that the temperature values in a time series representing the user's temperature over time are lower than a pregnancy baseline of temperature values for the user. The indication of the early pregnancy loss for the user may be identified and/or predicted by leveraging temperature sensors on the ring 104 of the system 200. In some cases, the indication of the early pregnancy loss may be estimated by identifying one or more morphological features such as deviations in the time series representing the user's temperature over time relative to the pregnancy baseline of temperature values and detecting the indication of early pregnancy loss that corresponds to the deviations of the time series. The indication of early pregnancy loss may be an example of identifying that the early pregnancy loss has already occurred, is currently occurring, and/or that the early pregnancy loss is predicted to occur in the future.

For example, as noted previously herein, the ring 104 of the system 200 may be worn by a user to collect data from the user, including temperature, heart rate, HRV, respiratory data, and the like. The ring 104 of the system 200 may collect the physiological data from the user based on temperature sensors and measurements extracted from arterial blood flow (e.g., using PPG signals). The physiological data may be collected continuously. In some implementations, the processing module 230-a may sample the user's temperature continuously throughout the day and night. Sampling at a sufficient rate (e.g., one sample per minute)

throughout the day and/or night may provide sufficient temperature data for analysis described herein. In some implementations, the ring 104 may continuously acquire temperature data (e.g., at a sampling rate). In some examples, even though temperature is collected continuously, the system 200 may leverage other information about the user that it has collected or otherwise derived (e.g., sleep stage, activity levels, illness onset, etc.) to select a representative temperature for a particular day that is an accurate representation of the underlying physiological phenomenon.

In contrast, systems that require a user to manually take their temperature each day and/or systems that measure temperature continuously but lack any other contextual information about the user may select inaccurate or inconsistent temperature values for their menstrual cycle predictions and/or pregnancy tracking, leading to inaccurate predictions and decreased user experience. In contrast, data collected by the ring 104 may be used to accurately detect the indication of the early pregnancy loss of the user. Early pregnancy loss identification and prediction and related techniques are further shown and described with reference to FIG. 3.

Figure 3:
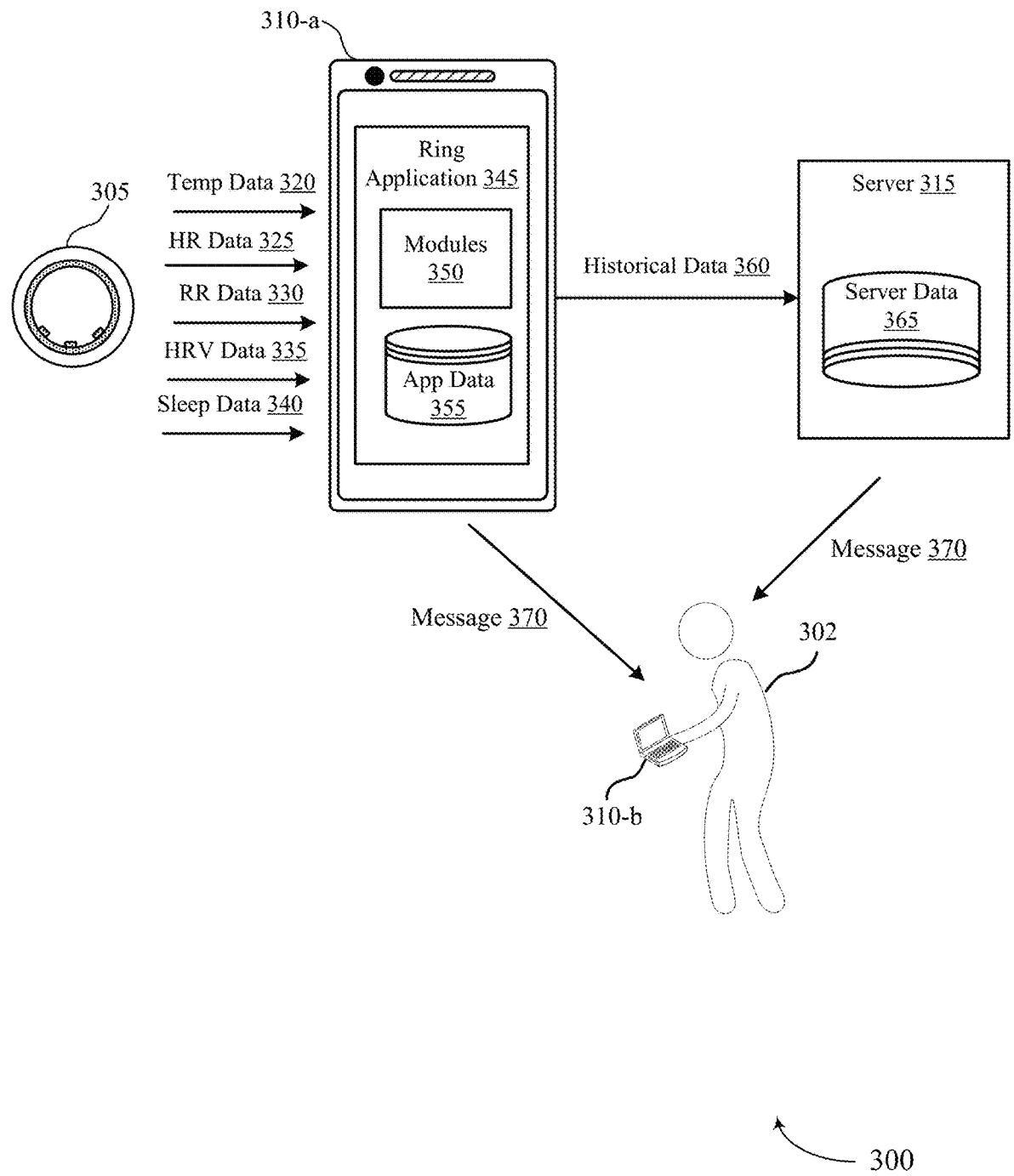
FIG. 3 illustrates an example of a system that supports miscarriage identification and prediction from wearable-based physiological data in accordance with aspects of the present disclosure.

FIG. 3 illustrates an example of a system 300 that supports miscarriage identification and prediction from wearable-based physiological data in accordance with aspects of the present disclosure. The system 300 may implement, or be implemented by, system 100, system 200, or both. In particular, system 300 illustrates an example of a ring 104 (e.g., wearable device 104), a user device 106, and a server 110, as described with reference to FIG. 1.

The ring 305 may acquire temperature data 320, heart rate data 325, respiratory rate data 330, HRV data 335, and sleep data 340, among other forms of physiological data as described herein. In such cases, the ring 305 may transmit temperature data 320, heart rate data 325, respiratory rate data 330, HRV data 335, and sleep data 340 to the user device 310. The temperature data 320 may include continuous nighttime temperature data. The respiratory rate data 330 may include continuous nighttime breath rate data. In some cases, multiple devices may acquire physiological data. For example, a first computing device (e.g., user device 310) and a second computing device (e.g., the ring 305) may acquire temperature data 320, heart rate data 325, respiratory rate data 330, HRV data 335, sleep data 340, or a combination thereof.

For example, the ring 305 may acquire user physiological data, such as user temperature data 320, respiratory rate data 330, heart rate data 325, HRV data 335, and sleep data 340, galvanic skin response, blood oxygen saturation, actigraphy, and/or other user physiological data. For example, the ring 305 may acquire raw data and convert the raw data to features with daily granularity. In some implementations, different granularity input data may be used. The ring 305 may send the data to another computing device, such as a mobile device (e.g., user device 310) for further processing.

For example, the user device 310 may identify and/or predict the indication of the early pregnancy loss based on the received data. In some cases, the system 300 may identify and/or predict the indication of the early pregnancy loss based on temperature data 320, respiratory rate data 330, heart rate data 325, HRV data 335, sleep data 340, galvanic skin response, blood oxygen saturation, activity, sleep architecture, or a combination thereof. In some cases, the system 300 may determine which features are useful predictors for early pregnancy losses. Although the system may be implemented by a ring 305 and a user device 310, any combination of computing devices described herein may implement the features attributed to the system 300.

The user device 310-a may include a ring application 345. The ring application 345 may include at least modules 350 and application data 355. In some cases, the application data 355 may include historical temperature patterns for the user and other data. The other data may include temperature data 320, heart rate data 325, respiratory rate data 330, HRV data 335, sleep data 340, or a combination thereof.

The ring application 345 may present a predicted and/or detected early pregnancy loss to the user. The ring application 345 may include an application data processing module that may perform data processing. For example, the application data processing module may include modules 350 that provide functions attributed to the system 300. Example modules 350 may include a daily temperature determination module, a time series processing module, a miscarriage identification module, and miscarriage prediction module.

The daily temperature determination module may determine daily temperature values (e.g., by selecting a representative temperature value for that day from a series of temperature values that were collected continuously throughout the night). The time series processing module may process time series data to identify that the plurality of temperature values are lower than a pregnancy baseline of temperature values. The miscarriage identification module may identify the indication of the early pregnancy loss of the user based on the processed time series data. The miscarriage prediction module may predict the indication of the early pregnancy loss of the user based on the processed time series data. In such cases, the system 300 may receive user physiological data (e.g., from a ring 305) and output daily classification of whether pregnancy loss is identified or predicted. The ring application 345 may store application data 355, such as acquired temperature data, other physiological data, pregnancy tracking data (e.g., event data), and miscarriage tracking data.

In some cases, the system 300 may generate pregnancy and/or miscarriage tracking data based on user physiological data (e.g., temperature data 320). The pregnancy and/or miscarriage tracking data may include a detected indication of the early pregnancy loss for the user, which may be determined based on acquired user temperature data (e.g., daily temperature data 320) over an analysis time period (e.g., a period of weeks/months). For example, the system 300 may receive physiological data associated with a user from a wearable device (e.g., ring 305). The physiological data may include at least temperature data 320, heart rate data 325, respiratory rate data 330, HRV data 335, sleep data 340, or a combination thereof. For example, the system 300 acquires user physiological data over an analysis time period (e.g., a plurality of days). In such cases, the system 300 may acquire and process user physiological data over an analysis time period to generate one or more time series of user physiological data.

In some cases, the system 300 may acquire daily user temperature data 320 over an analysis time period. For example, the system 300 may calculate a single temperature value for each day. The system 300 may acquire a plurality of temperature values during the night and process the acquired temperature values to determine the single daily temperature value. In some implementations, the system 300 may determine a time series of a plurality of temperature values taken over a plurality of days based on the received temperature data 320. The system 300 may detect the indication of the early pregnancy loss in the time series of the temperature values based on identifying that the plurality of temperature values are lower than a pregnancy baseline of temperature values for the user, as further shown and described with reference to FIG. 5.

In some implementations, the system 300 may determine that the received heart rate data 325 exceeds a pregnancy baseline heart rate for the user for at least a portion of the plurality of days. In such cases, the system 300 may detect the indication of the early pregnancy loss based on determining that the received heart rate data 325 exceeds the pregnancy baseline heart rate for the user. In some examples, the system 300 may determine that the received respiratory rate data 330 exceeds a pregnancy baseline respiratory rate for the user for at least a portion of the plurality of days. In such cases, the system 300 may detect the indication of the early pregnancy loss based on determining that the received respiratory rate data 330 exceeds the pregnancy baseline respiratory rate for the user.

In some implementations, the system 300 may determine that the received HRV data 335 is less than a pregnancy baseline HRV for the user for at least a portion of the plurality of days. In such cases, the system 300 may detect the indication of the early pregnancy loss based on determining that the received HRV data 335 is less than a pregnancy baseline HRV for the user. In some implementations, the system 300 may determine that a quantity of detected sleep disturbances from the received sleep data 340 exceeds a pregnancy baseline sleep disturbance threshold for the user for at least a portion of the plurality of days. In such cases, the system 300 may detect the indication of the early pregnancy loss based on determining that the quantity of detected sleep disturbances from the received sleep data 340 exceeds a pregnancy baseline sleep disturbance threshold for the user. In such cases, the pregnancy baselines (e.g., temperature, heart rate, respiratory rate, HRV, sleep data, and the like) may be tailored-specific to the user based on historical data 360 acquired by the system 300. For example, these pregnancy baselines may represent baseline or average values of physiological parameters or typical trends of physiological values throughout a user's pregnancy, which may differ from the user's normal or non-pregnant baselines. In some cases, the pregnancy baselines may differ throughout the user's pregnancy (e.g., based on the different stages of pregnancy) for each physiological parameter. In some cases, the pregnancy baselines may be based on known standards, averages among users, demographic-specific, and/or based on a user's prior pregnancies.

In some cases, one or more physiological measurements may be combined to detect the indication of the early pregnancy loss. In such cases, identifying the indication of the pregnancy loss may be based on one physiological measurement or a combination of physiological measurements (e.g., temperature data 320, heart rate data 325, respiratory rate data 330, HRV data 335, sleep data 340). For example, the user's heart rate data 325 in combination with the user's temperature data 320 may be an indicator that may characterize an early pregnancy loss. In some cases, the user's heart rate data 325 may confirm (e.g., provide a definitive indication of or better prediction of) the indication of the early pregnancy loss in light of the user's temperature data 320. For example, if the system 300 determines that the received heart rate data 325 exceeds the pregnancy baseline heart rate for the user and that the received temperature data 320 is greater than the pregnancy baseline temperature for the user, the system 300 may validate or detect the indication of the early pregnancy loss with greater accuracy and precision than if one of the heart rate data 325 or temperature data 320 deviates from the pregnancy baseline.

In some examples, one or more physiological measurements may be combined to disprove or reduce the likelihood of a detected indication of the early pregnancy loss. In such cases, the system 300 may identify a false positive for identifying the indication of the early pregnancy loss based on one physiological measurement or a combination of physiological measurements. For example, if the system 300 determines that the received temperature data 320 is greater than the pregnancy baseline temperature for the user but the received respiratory rate data 330 still aligns with the pregnancy baseline respiratory rate for the user, the system 300 may determine that the detected indication of the early pregnancy loss is invalid or at least less likely than if both the temperate and respiratory rate deviated from their pregnancy baselines. In such cases, the system 300 may determine that the user may be experiencing an illness, hormonal shift in the menstrual cycle, and the like.

In some cases, the user's logged symptoms (e.g., tags) in combination with the user's physiological data (e.g., temperature data 320, heart rate data 325, respiratory rate data 330, HRV data 335, sleep data 340, or a combination thereof) may be an indicator that may characterize an indication of the early pregnancy loss. In such cases, the user's logged symptoms may confirm (e.g., provide a definitive indication of or better prediction of) the indication of the early pregnancy loss in light of the user's physiological data. For example, if the system 300 determines that the received temperature data 320 is greater than the pregnancy baseline temperature for the user and the system receives user input associated with a miscarriage (e.g., bleeding, pain, etc.), the system may validate or detect the indication of the early pregnancy loss with greater accuracy and precision than if one of the temperature data 320 deviates from the pregnancy baseline or the user logs early pregnancy loss symptoms.

In some examples, the system 300 may identify a false positive for identifying the indication of the early pregnancy loss based on the user input, one physiological measurement, a combination of physiological measurements, or a combination thereof. For example, if the system 300 determines that the received heart rate data 325 is greater than the pregnancy baseline heart rate for the user but the user input indicates a symptom associated with stress, illness, anxiety, a change in medication, and the like, the system 300 may determine that the detected indication of early pregnancy loss is invalid (e.g., a false positive). In such cases, the system 300 may determine that the user may be experiencing an illness, stress, hormonal shift in the menstrual cycle, and the like based on receiving the user input.

In some implementations, the system may identify personalized lifestyle factors to improve fertility treatment success. For example, the system may track behavioral metrics related to sleep, activity, and nutrition to help users improve fertility and guide fertility treatment. In some cases, there may be a relationship between sleep disturbance and reproductive health (e.g., whether the user experiences a miscarriage during pregnancy). Sleep disturbance may be detected in users such as users under stress and/or shift workers that experience sleep disruption and circadian misalignment impacting reproductive health outcomes including: menstrual irregularities, dysmenorrhea, reduced rates of conception, increased miscarriages, and lower birth weights. By monitoring sleep data for the user and aggregate users undergoing fertility treatments, the system 300 may provide valuable insights into the relationship between various dimensions and metrics of sleep and fertility in order to increase successful pregnancy rates.

In some implementations, the system 300 may ask a user to indicate whether they are shift workers (e.g., during a sign-up process) or experience other sleep disturbances. In such cases, metrics (e.g., self-reported and signal-derived metrics of circadian disruption) may be incorporated as features in a machine learning model to predict risk for subfertility, infertility, fertility treatment success, fertility complications, the likelihood of miscarriage, or a combination thereof. The system 300 that considers the user's sleep history and quantifies the magnitude of circadian disruption may surface tags that may provide input on overall health as well as fertility status (e.g., late night meal, back pain, chest pain). In some implementations, these factors may be used to drive the selection and personalization of insights displayed to the users. The system 300 may provide feedback on fertility odds while considering menstrual cycle irregularities. For example, the user may be provided with information related to circadian rhythms and sleep hygiene. The user may be presented the option to connect with a human-in-the-loop live sleep coach to set goals and an action plan that may lead to application supported behavioral changes under the user's personal constraints and limitations (e.g., time, nutrition). In some implementations, the system 300 may allow users to tag melatonin and see related changes in sleep and fertility, as melatonin levels and supplementation may influence fertility outcomes (e.g., via biological mechanisms such as reduction of oxidative stress-mediated effects on reproductive tissues).

The system 300 may cause a GUI of the user devices 310-a, 310-b to display the indication of the early pregnancy loss. In some cases, the system 300 may cause the GUI to display the time series. The system 300 may generate a tracking GUI that includes physiological data (e.g., at least temperature data 320), tagged events, and/or other GUI elements described herein with reference to FIG. 4. In such cases, the system 300 may render ovulations, periods, pregnancy, a miscarriage, and the like in a tracking GUI.

The system 300 may generate a message 370 for display on a GUI on a user device 310-a or 310-b that indicates the indication of the early pregnancy loss. For example, the system 300 (e.g., user device 310-a or server 315) may transmit the message 370 that indicates the predicted and/or identified early pregnancy loss to the user device 310-b. In such cases, the user device 310-b may be associated with a clinician, a fertility specialist, a care-taker, a partner, or a combination thereof. The detection of a probable pregnancy loss may trigger a personalized message 370 to a user highlighting the pattern detected in the temperature data and providing an educational link about pregnancy loss.

In some implementations, the ring application 345 may notify the user of indication of early pregnancy loss and/or prompt the user to perform a variety of tasks in the activity GUI. The notifications and prompts may include text, graphics, and/or other user interface elements. The notifications and prompts may be included in the ring application 345 such as when there is identified and/or predicted pregnancy loss, the ring application 345 may display notifications and prompts. The user device 310 may display notifications and prompts in a separate window on the home screen and/or overlaid onto other screens (e.g., at the very top of the home screen). In some cases, the user device 310 may display the notifications and prompts on a mobile device, a user's watch device, or both.

In some examples, the system 300 provide mitigation advice. In such cases, the system 300 may provide recommendations on steps to take to confirm or disprove the indication of the early pregnancy loss. For example, if the system 300 determines that the user's respiratory rate is elevated above the pregnancy baseline heart rate, the system 300 may prompt the user to perform a meditation and/or breathing exercise a few times a day for a couple of days and the re-evaluate the respiratory rate data 330. In such cases, the system 300 may receive the physiological data after the user performs the mitigation advice to determine whether the user is experiencing a miscarriage, if the user is experiencing a period of anxiety, or both.

In some implementations, the user device 310 may store historical user data. In some cases, the historical user data may include historical data 360. The historical data 360 may include historical temperature patterns of the user, historical heart rate patterns of the user, historical respiratory rate patterns of the user, historical HRV patterns of the user, historical sleep patterns of the user, historical menstrual cycle onset events (e.g., cycle length, cycle start date, etc.) of the user, or a combination thereof. The historical data 360 may be selected from the last few months. The historical data 360 may be used (e.g., by the user device 310 or server 315) to determine a threshold (e.g., pregnancy baseline) for the user, determine temperature values of the user, predict an early pregnancy loss, identify an early pregnancy loss, or a combination thereof. The historical data 360 may be used by the server 315. Using the historical data 360 may allow the user device 310 and/or server 315 to personalize the GUI by taking into consideration user's historical data 360.

In such cases, the user device 310 may transmit historical data 360 to the server 315. In some cases, the transmitted historical data 360 may be the same historical data stored in the ring application 345. In other examples, the historical data 360 may be different than the historical data stored in the ring application 345. The server 315 may receive the historical data 360. The server 315 may store the historical data 360 in server data 365.

In some implementations, the user device 310 and/or server 315 may also store other data which may be an example of user information. The user information may include, but is not limited to, user age, weight, height, and gender. In some implementations, the user information may be used as features for predicting or identifying early pregnancy loss. The server data 365 may include the other data such as user information.

In some implementations, the system 300 may include one or more user devices 310 for different users. For example, the system 300 may include user device 310-a for a primary user and user device 310-b for a second user 302 associated with the primary user (e.g., partner). The user devices 310 may measure physiological parameters of the different users, provide GUIs for the different users, and receive user input from the different users. In some implementations, the different user devices 310 may acquire physiological information and provide output related to a woman's health, such as menstrual cycles, ovarian cycles, illness, fertility, and/or pregnancy. In some implementations, the user device 310-b may acquire physiological information related to the second user 302, such as male illness and fertility.

In some implementations, the system 300 may provide GUIs that inform the second user 302 of relevant information. For example, the first user and the second user 302 may share their information with one another via one or more user devices 310, such as via a server device, mobile device, or other device. In some implementations, the second user 302 may share one or more of their accounts (e.g., usernames, login information, etc.) and/or associated data with one another (e.g., the first user). By sharing information between users, the system 300 may assist second users 302 in making health decisions related to pregnancy. In some implementations, the users may be prompted (e.g., in a GUI) to share specific information. For example, the user may use a GUI to opt into sharing her pregnancy information with the second user 302. In such cases, the user and the second user 302 may receive notifications on their respective user devices 310. In other examples, a second user 302 may make their information (e.g., illness, pregnancy data, etc.) available to the user via a notification or other sharing arrangement. In such cases, the second user 302 may be an example of a clinician, a fertility specialist, a care-taker, a partner, or a combination thereof.

Figure 4:
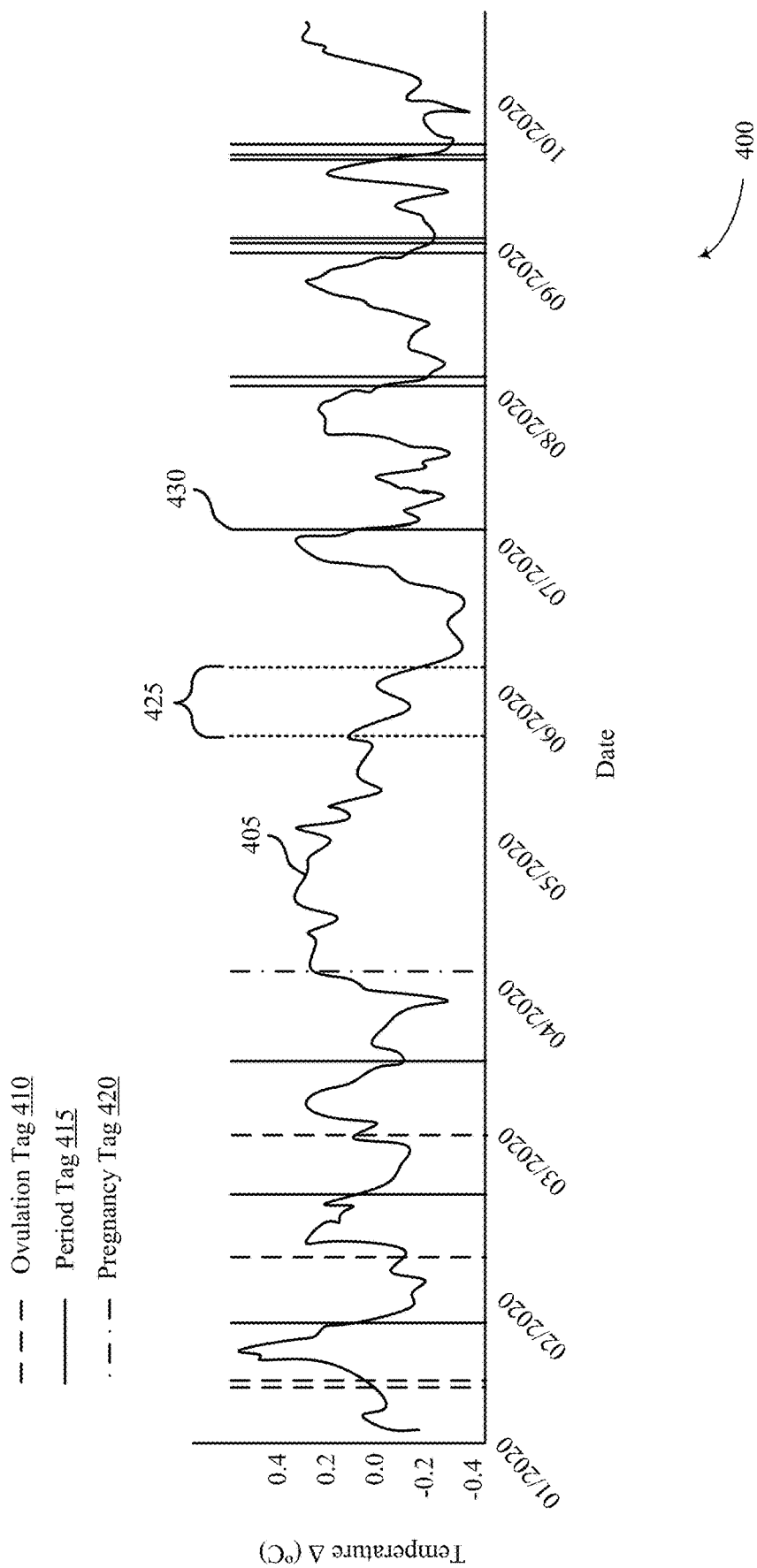
FIG. 4 illustrates an example of a timing diagram that supports miscarriage identification and prediction from wearable-based physiological data in accordance with aspects of the present disclosure.

FIG. 4 illustrates an example of a timing diagram 400 that supports miscarriage identification and prediction from wearable-based physiological data in accordance with aspects of the present disclosure. The timing diagrams 400 may implement, or be implemented by, aspects of the system 100, system 200, system 300, or a combination thereof. For example, in some implementations, the timing diagram 400 may be displayed to a user via the GUI 275 of the user device 106, as shown in FIG. 2.

As described in further detail herein, the system may be configured to identify and predict a miscarriage. In some cases, the user's body temperature pattern throughout the day and night may be an indicator that may characterize a miscarriage. For example, skin temperature during the day and night may identify and/or predict a miscarriage (e.g., early pregnancy loss). As such, the timing diagram 400 illustrates a relationship between a user's temperature data and a time (e.g., over a plurality of months). In this regard, the solid curved line illustrated in the timing diagram 400 may be understood to refer to the "temperature values 405." The dashed vertical line illustrated in the timing diagram 400 may be understood to refer to the "ovulation tag 410." The dashed-dotted vertical line illustrated in the timing diagram 400 may be understood to refer to the "pregnancy tag 420." The solid vertical bars illustrated in the timing diagram 400 may be understood to refer to the "period tag 415." The user's temperature values 405 may be relative to a baseline temperature.

In some cases, the system (e.g., ring 104, user device 106, server 110) may receive physiological data associated with a user from a wearable device. The physiological data may include at least temperature data. The system may determine a time series of temperature values 405 taken over a plurality of days based on the received temperature data. With reference to timing diagram 400, the plurality of days may be an example of ten months. The system may process original time series temperature data (e.g., temperature values 405) to detect the indication of the early pregnancy loss 425. In some cases, the time series may include a plurality of events tagged by the user in the system. For example, the time series may include ovulation tags 410, period tags 415, and a pregnancy tag 420. In some cases, the ovulation tags 410, period tags 415, and a pregnancy tag 420 may be determined by the system based on physiological data continuously collected by the system.

The temperature values 405 may be continuously collected by the wearable device. The physiological measurements may be taken continuously throughout the day and/or night. For example, in some implementations, the ring may be configured to acquire physiological data (e.g., temperature data, sleep data, heart rate, HRV data, respiratory rate data, sleep data, MET data, and the like) continuously in accordance with one or more measurement periodicities throughout the entirety of each day/sleep day. In other words, the ring may continuously acquire physiological data from the user without regard to "trigger conditions" for performing such measurements. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body or if the user were manually taking their temperature once per day.

In some implementations, the system may detect the indication of the early pregnancy loss 425 by observing a user's relative body temperature for many days and marking the decrease in temperature relative to a pregnancy baseline, which may indicate a miscarriage (e.g., early pregnancy loss). The indication of the early pregnancy loss 425 may include a duration of time (e.g., time span) including at least a day, a plurality of days, a week, a plurality of weeks, or a month. In such cases, the indication of the early pregnancy loss 425 may include a start date and an end date. The indication of the early pregnancy loss 425 may be an example of a detected miscarriage that previously occurred or currently occurs and/or a predicted miscarriage that likely occurs in the future.

The system may detect the indication of the early pregnancy loss 425 in the time series of the temperature values 405 based on identifying that the temperature values 405 are lower than a pregnancy baseline of temperature values for the user. For example, the system may identify the temperature values 405 after determining the time series and identify the pregnancy baseline of temperature values. The system may detect the indication of the early pregnancy loss 425 of the user in response to identifying that the temperature values 405 are lower than the pregnancy baseline of temperature values for the user.

As described in further detail herein, the system may be configured to track menstrual cycles, ovulation, pregnancy, miscarriage, and the like. In some cases, the user's body temperature pattern throughout the night may be an indicator that may characterize miscarriage. For example, skin temperature during the night may identify the indication of the early pregnancy loss 425. As such, the timing diagram 400 illustrates a relationship between a user's temperature data and a time (e.g., over a plurality of months).

The timing diagram 400 may illustrate a user with three periods (e.g., period tags 415), an indication of pregnancy (e.g., pregnancy tag 420), the indication of the early pregnancy loss 425, followed by at least four more menstrual cycles (e.g. period tags 415). For example, the timing diagram 400 may indicate that the miscarriage occurred after 2 months (e.g., eight weeks) from the pregnancy tag 420. The timing diagram 400 may indicate a user who had several periods (e.g., period tags 415) that may have been identified automatically and/or by user tags in the application. For example, timing diagram 400 illustrates that the user became pregnant (e.g., indicated via pregnancy tag 420) and then returned to having periods (e.g., automatically detected or tagged via period tags 415) within less than 9 months after becoming pregnant, thereby indicating the user likely had a miscarriage. The user's temperature trajectory around the time of the pregnancy tag 420 may be not much higher than the temperature peak at the time of the period tags 415. In such cases, the system may determine that the temperature trajectory of the user may peak (e.g., thereby indicating a period) within less than 9 months after becoming pregnant such that the system may determine that the user is likely experiencing a miscarriage.

In some cases, the system may identify a presence of a menstrual cycle 430 within a time period after pregnancy onset (e.g., pregnancy tag 420) based on determining the time series. In such cases, the indication of the early pregnancy loss 425 may be detected based on identifying the presence of the menstrual cycle 430. For example, if the system identifies the menstrual cycle 430 within 20 weeks of the pregnancy tag 420, the system may detect the indication of the early pregnancy loss 425. The menstrual cycle 430 may be identified based on the user's continuously collected physiological data, a received confirmation, or both. For example, the system may receive a confirmation of a menstrual cycle 430 within a time period after the pregnancy tag 420. In some cases, the system may receive a confirmation of a pregnancy loss. In such cases, the system may detect the indication of the early pregnancy loss 425 in response to receiving the confirmation of the menstrual cycle 430, the pregnancy loss, or both.

Figure 5:
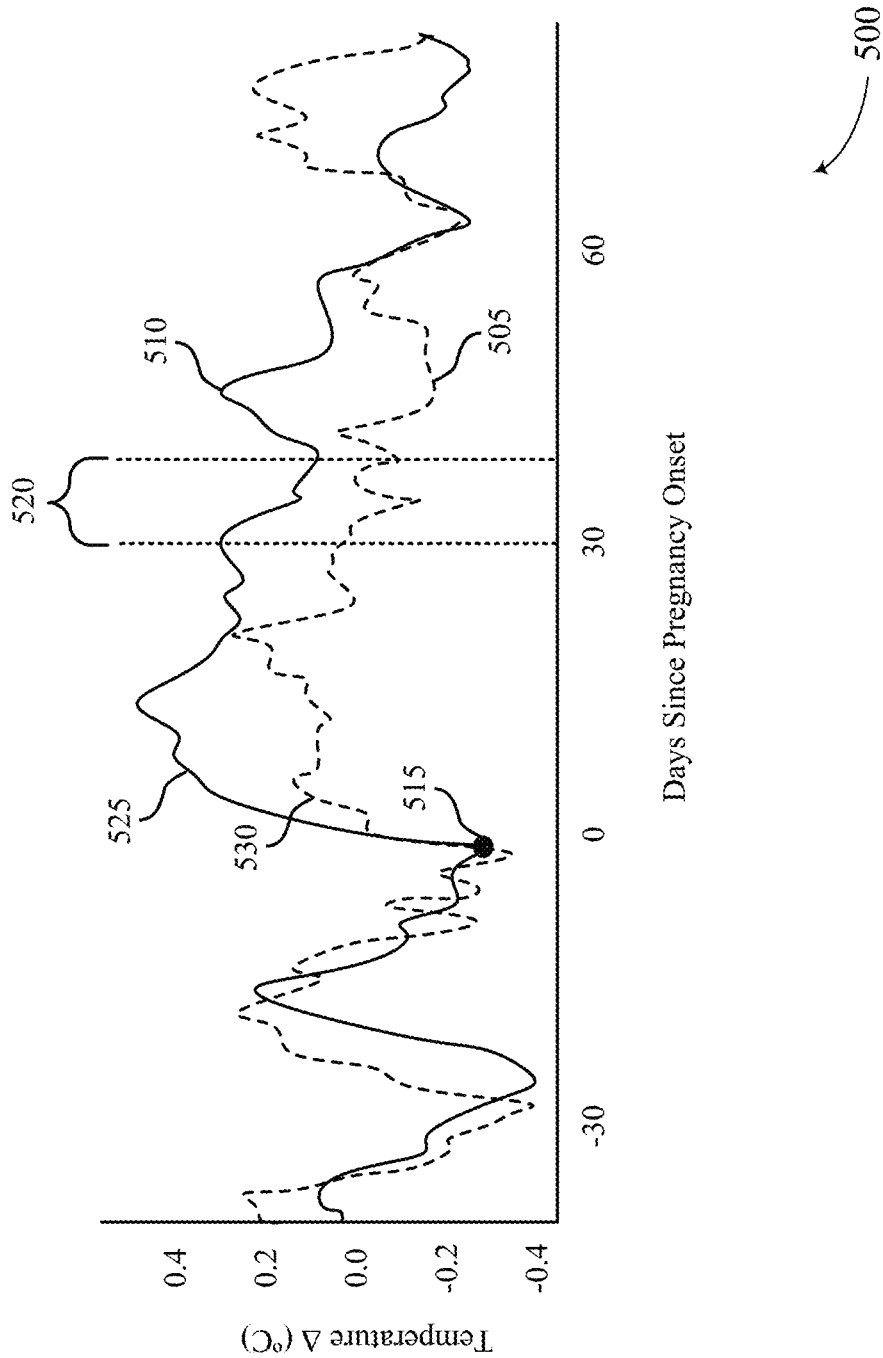
FIG. 5 illustrates an example of a timing diagram that supports miscarriage identification and prediction from wearable-based physiological data in accordance with aspects of the present disclosure.

FIG. 5 illustrates an example of a timing diagram 500 that supports miscarriage identification and prediction from wearable-based physiological data in accordance with aspects of the present disclosure. The timing diagram 500 may implement, or be implemented by, aspects of the system 100, system 200, system 300, or a combination thereof. For example, in some implementations, the timing diagram 500 may be displayed to a user via the GUI 275 of the user device 106, as shown in FIG. 2.

As described in further detail herein, the system may be configured to identify and predict a miscarriage based on deviations relative to a pregnancy baseline. In some cases, the user's body temperature pattern throughout the night may be an indicator that may characterize a miscarriage. For example, skin temperature during the day and/or night may identify and/or predict a miscarriage (e.g., early pregnancy loss). As such, the timing diagram 500 illustrates a relationship between a user's temperature data and a time (e.g., over a plurality of days relative to pregnancy). In this regard, the dashed curved line illustrated in the timing diagram 500 may be understood to refer to the "temperature values 505." In this regard, the solid curved line illustrated in the timing diagram 500 may be understood to refer to the "pregnancy baseline of temperature values 510." The user's temperature values 505 and pregnancy baseline of temperature values 510 may be relative to a baseline temperature.

In some cases, the system (e.g., ring 104, user device 106, server 110) may receive physiological data associated with a user from a wearable device. The physiological data may include at least temperature values 505. The system may determine a time series of the temperature values 505 taken over a plurality of days based on the received temperature data. With reference to timing diagram 500, the plurality of days may be an example of at least three months (e.g., one month prior to pregnancy onset and two months after pregnancy onset). The system may process original time series temperature data (e.g., temperature values 505) to detect the indication of an early pregnancy loss 520. In some cases, the time series may include a plurality of events tagged by the user in the system. For example, the time series may include an indication of pregnancy 515. In some cases, indication of pregnancy 515 may be determined by the system based on physiological data continuously collected by the system, based on a user input, or both.

The temperature values 505 may be continuously collected by the wearable device. The physiological measurements may be taken continuously throughout the night. For example, in some implementations, the ring may be configured to acquire physiological data (e.g., temperature data, sleep data, heart rate, HRV data, respiratory rate data, MET data, sleep data, and the like) continuously in accordance with one or more measurement periodicities throughout the entirety of each day/sleep day. In other words, the ring may continuously acquire physiological data from the user without regard to "trigger conditions" for performing such measurements. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body or if the user were manually taking their temperature once per day.

In some implementations, the system may identify and/or predict the indication of the early pregnancy loss 520 by observing a user's relative body temperature for many days and marking the decrease in temperature relative to a pregnancy baseline (e.g., pregnancy baseline of temperature values 510), which may indicate a miscarriage. The indication of the early pregnancy loss 520 may include a duration of time (e.g., time span) including at least a day, a plurality of days, a week, or a plurality of weeks. In such cases, the indication of the early pregnancy loss 520 may include a start date and an end date. The indication of the early pregnancy loss 520 may be an example of a detected miscarriage that previously occurred or currently occurs and/or a predicted miscarriage that likely occurs in the future.

The system may identify and/or predict the indication of the early pregnancy loss 520 in the time series of the temperature values 505 based on identifying that the temperature values 505 are lower than the pregnancy baseline of temperature values 510 for the user. For example, the system may identify the temperature values 505 after determining the time series and identify the pregnancy baseline of temperature values 510. The system may detect the indication of the early pregnancy loss 520 of the user in response to identifying that the temperature values 505 are lower than the pregnancy baseline of temperature values 510 for the user.

In some cases, the temperature values 505 may deviate from the pregnancy baseline of temperature values 510 for the user after the indication of pregnancy 515. For example, after identifying the indication of pregnancy 515, the system may determine that the temperature values 505 deviation from (e.g., are less than) the pregnancy baseline of temperature values 510. The system may compute a deviation in the time series of the temperature values 505 relative to the pregnancy baseline of temperature values 510 for the user in response to determining the time series. The deviation may include a decrease in the temperature values 505 from the pregnancy baseline of temperature values 510 for the user. In such cases, identifying that the temperature values 505 are lower than the pregnancy baseline of temperature values 510 is in response to computing the deviation.

In some cases, the system may determine, or estimate, the temperature maximum and/or minimum for a user after determining the time series of the temperature values 505 for the user collected via the ring. The system may identify the one or more positive slopes 530 of the time series of the temperature values 505 based on determining the maximum and/or minimum. In some cases, calculating the difference between the maximum and minimum may determine the positive slope 530. In other examples, identifying the one or more positive slopes 530 of the time series of the temperature values 505 may be in response to computing a derivative of the original time series temperature data (e.g., temperature values 505).

The system may identify the one or more positive slopes 525 of the time series of the pregnancy baseline of temperature values 510 based on determining the maximum and/or minimum. In some cases, calculating the difference between the maximum and minimum may determine the positive slope 525. In other examples, identifying the one or more positive slopes 525 of the time series of the pregnancy baseline of temperature values 510 may be in response to computing a derivative of the pregnancy baseline of temperature values 510.

In some implementations, the system may identify that one or more positive slopes 530 of the temperature values 505 are lower than a positive slope 525 for a pregnancy baseline of temperature values 510 for the user in response to determining the time series. For example, the slope 530 of the temperature values 505 may be below the slope 525 of the pregnancy baseline of temperature values 510 for the user. In some cases, the degree (e.g., angle of slope) of the slope 530 of the temperature values 505 may be less than the degree of the slope 525 of the pregnancy baseline of temperature values 510 for the user. In such cases, identifying that the temperature values 505 are lower than the pregnancy baseline of temperature values 510 for the user is in response to identifying that the one or more positive slopes 530 are lower than the positive slope 525 for the pregnancy baseline of temperature values 510 for the user. For example, the temperature rise is lower and the temperature decrease occurs earlier for the temperature values 505 as compared to the pregnancy baseline of temperature values 510 for the user. In such cases, the temperature patterns for a user experiencing or predicted to experience a miscarriage is different than a temperature pattern for a user experiencing a full-term pregnancy.

As described in further detail herein, the system may be configured to track menstrual cycles, ovulation, pregnancy, and the like. In some cases, the user's body temperature pattern throughout the night may be an indicator that may characterize miscarriage. For example, skin temperature during the night may identify the indication of the early pregnancy loss 520. As such, the timing diagram 500 illustrates a relationship between a user's temperature data and a time (e.g., over a plurality of months).

In some cases, the system may estimate a likelihood of future early pregnancy loss 520, a likelihood that the user will experience the early pregnancy loss 520, or both, in response to identifying that the temperature values 505 are lower than the pregnancy baseline of temperature values 510 for the user. In such cases, the system may predict the indication of the early pregnancy loss 520, detect the indication of the early pregnancy loss 520, or both.

Figure 6:
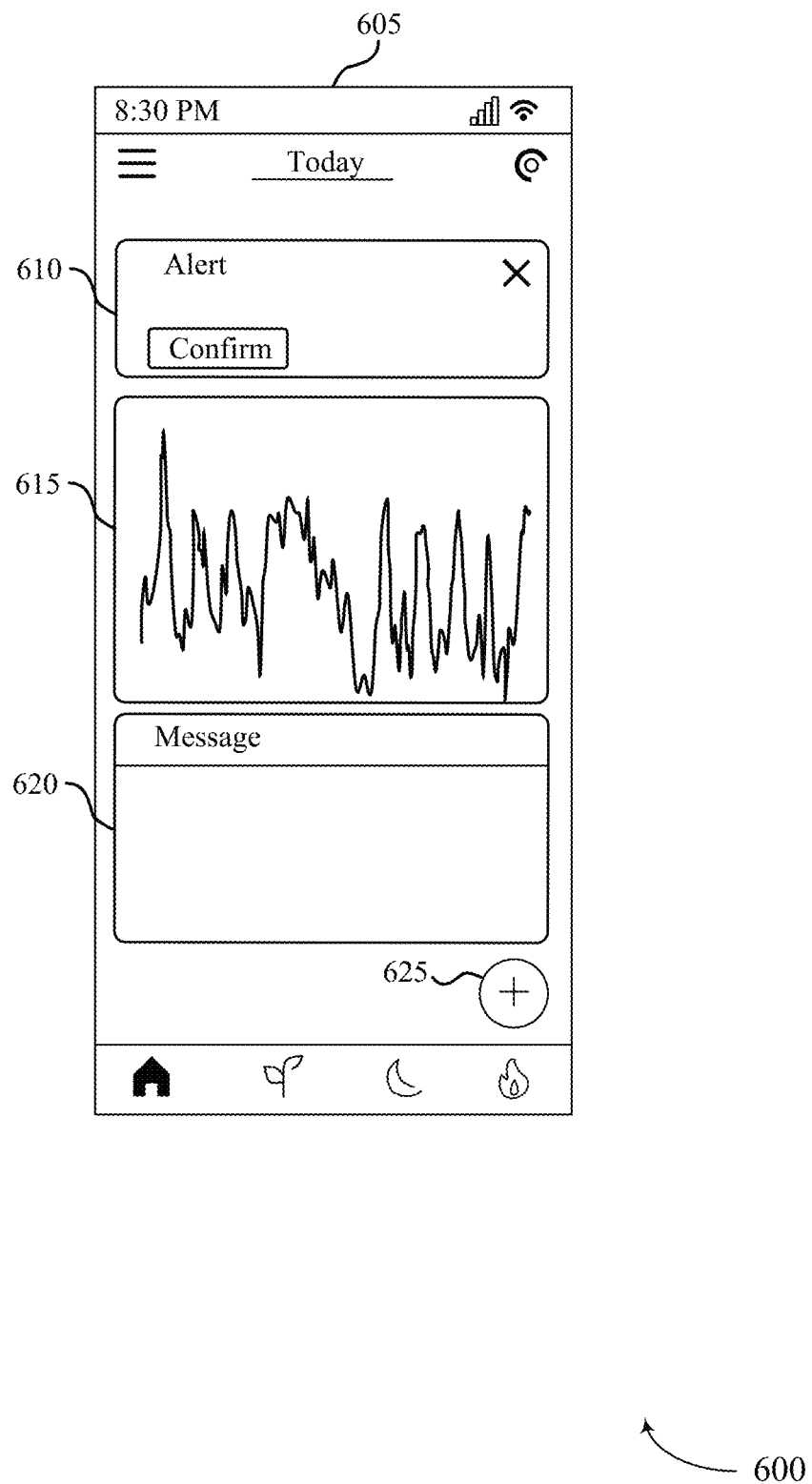
FIG. 6 illustrates an example of a graphical user interface (GUI) that supports miscarriage identification and prediction from wearable-based physiological data in accordance with aspects of the present disclosure.

FIG. 6 illustrates an example of a GUI 600 that supports miscarriage identification and prediction from wearable-based physiological data in accordance with aspects of the present disclosure. The GUI 600 may implement, or be implemented by, aspects of the system 100, system 200, system 300, timing diagram 400, timing diagram 500, or any combination thereof. For example, the GUI 600 may be an example of a GUI 275 of a user device 106 (e.g., user device 106-a, 106-b, 106-c) corresponding to a user 102.

In some examples, the GUI 600 illustrates a series of application pages 605 which may be displayed to a user via the GUI 600 (e.g., GUI 275 illustrated in FIG. 2). The server of the system may cause the GUI 600 of the user device (e.g., mobile device) to display inquiries of whether the user activates the pregnancy mode and wants to track their pregnancy (e.g., via application page 605). In such cases, the system may generate a personalized tracking experience on the GUI 600 of the user device to predict a risk for pregnancy loss or detect when the pregnancy is no longer viable based on the contextual tags and user questions.

Continuing with the examples above, prior to detecting the indication of the early pregnancy loss of the user, the user may be presented with an application page upon opening the wearable application. The application page 605 may display a request to activate the pregnancy mode and enable the system to track the pregnancy. In such cases, the application page 605 may display an invitation card where the users are invited to enroll in the pregnancy tracking applications. The application page 605 may display a prompt to the user to verify whether the pregnancy may be tracked or dismiss the message if the pregnancy is not tracked. The system may receive an indication of whether the user selects to opt-in to tracking the pregnancy or opt-out to tracking the pregnancy.

The user may be presented with an application page 605 upon selecting "yes" to tracking the pregnancy. The application page 605 may display a prompt to the user to verify the main reason to track pregnancy. In such cases, the application page 605 may prompt the user to confirm the intent of tracking the pregnancy. For example, the system may receive, via the user device, a confirmation of the intended use of the pregnancy tracking system.

In some cases, the user may be presented with an application page 605 upon confirming the intent. The application page 605 may display a prompt to the user to verify the day of conception, the due date, and the like. For example, the system may receive, via the user device, a confirmation of the due date. In some cases, the application page 605 may display a prompt to the user to indicate whether due date may not be determined.

In some cases, the user may be presented with an application page 605 upon confirming the due date. The application page may display a prompt to the user to verify whether the user experience any pregnancy-related complications, any pre-existing medical conditions, any fertility treatments used to achieve pregnancy, any sleep disturbances of the use (e.g., whether the user is a shift worker), and the like. For example, the system may receive, via the user device, a confirmation of whether the user experience any pregnancy-related complications, any pre-existing medical conditions, any fertility treatments used to achieve pregnancy, any sleep disturbances of the use (e.g., whether the user is a shift worker), and the like. Upon receiving the confirmations, the user may be presented with a GUI 600 that may be further shown and described with reference to application page 605.

The server of the system may generate a message for display on the GUI 600 on a user device that indicates the indication of the early pregnancy loss. For example, the server of system may cause the GUI 600 of the user device (e.g., mobile device) to display a message 620 associated with the indication of the early pregnancy loss (e.g., via application page 605). In such cases, the system may output the indication of the early pregnancy loss on the GUI 600 of the user device to indicate that the pregnancy is no longer viable, that the user is experiencing a risk of pregnancy loss, and/or a pregnancy loss is predicted for the future.

Continuing with the example above, upon detecting the indication of the early pregnancy loss of the user, the user may be presented with the application page 605 upon opening the wearable application. As shown in FIG. 6, the application page 605 may display the indication that the early pregnancy loss is predicted and/or identified via message 620. In such cases, the application page 605 may include the message 620 on the home page. In cases where a user's early pregnancy loss is predicted and/or identified, as described herein, the server may transmit a message 620 to the user, where the message 620 is associated with the predicted and/or identified early pregnancy loss. In some cases, the server may transmit a message 620 to a clinician, a fertility specialist, a care-taker, a partner of the user, or a combination thereof. In such cases, the system may present application page 605 on the user device associated with the clinician, the fertility specialists, the care-taker, the partner, or a combination thereof.

For example, the user may receive message 620, which may indicate a time interval during which the early pregnancy loss occurred, a time interval during which the early pregnancy loss is predicted to occur, a request to input symptoms associated with the early pregnancy loss, educational content associated with the early pregnancy loss, an adjusted set of sleep targets, an adjusted set of activity targets, recommendations to improve symptoms associated with the early pregnancy loss, and the like. For example, the message 620 may indicate a risk for pregnancy loss. The messages 620 may be configurable/customizable, such that the user may receive different messages 620 based on the prediction and identification of the early pregnancy loss, as described previously herein.

As shown in FIG. 6, the application page 605 may display the indication of the early pregnancy loss via alert 610. The user may receive alert 610, which may prompt the user to verify whether the early pregnancy loss has occurred or dismiss the alert 610 if the early pregnancy loss has not occurred. In such cases, the application page 605 may prompt the user to confirm or dismiss the early pregnancy loss (e.g., confirm/deny whether the system correctly detected the indication of the early pregnancy loss and/or confirm/deny whether the pregnancy loss has been confirmed via a clinician). For example, the system may receive, via the user device and in response to detecting the indication of the early pregnancy loss, a confirmation of the pregnancy loss.

Additionally, in some implementations, the application page 605 may display one or more scores (e.g., Sleep Score, Readiness Score, etc.) for the user for the respective day. Moreover, in some cases, the predicted and/or identified pregnancy loss may be used to update (e.g., modify) one or more scores associated with the user (e.g., Sleep Score, Readiness Score, etc.). That is, data associated with the predicted and/or identified pregnancy loss may be used to update the scores for the user for the following calendar days. In such cases, the system may notify the user of the score update via alert 610.

In some cases, the Readiness Score may be updated based on the detected indication of the early pregnancy loss. In such cases, the Readiness Score may indicate to the user to "pay attention" based on the predicted and/or identified early pregnancy loss. If the Readiness Score changes for the user, the system may implement a recovery mode for users whose symptoms may be severe and may benefit from adjusted activity and readiness guidance for a couple of days. In other examples, the Readiness Score may be updated based on the Sleep Score. However, the system may determine that the user is experiencing a miscarriage or predicted to experience a miscarriage and may adjust the Readiness Score, Sleep Score, and/or Activity Score to offset the effects of the miscarriage.

In some cases, the messages 620 displayed to the user via the GUI 600 of the user device may indicate how the predicted and/or identified early pregnancy loss affected the overall scores (e.g., overall Readiness Score) and/or the individual contributing factors. For example, a message may indicate "It looks like your body is under strain right now, but if you're feeling ok, doing a light or medium intensity exercise can help your body battle the symptoms" or "From your recovery metrics it looks like your body is still doing ok, so some light activity can help relieve the symptoms. Hope you'll feel better tomorrow!" In cases where the early pregnancy loss is predicted and/or identified, the messages 620 may provide suggestions for the user in order to improve their general health based on user history of the user, a group of users, general knowledge, or a combination thereof. For example, the message may indicate "If you feel really low on energy, why not switch to rest mode for today," or "Since you have cramps and pain, devote today for rest." In such cases, the messages 620 displayed to the user may provide targeted insights to help the user adjust their lifestyle.

The application page 605 may indicate one or more parameters, including a temperature, heart rate, HRV, respiratory rate, sleep data, and the like experienced by the user during the pregnancy loss via the graphical representation 615. The graphical representation 615 may be an example of the timing diagram 400, as described with reference to FIG. 4. In such cases, the system may cause the GUI 600 of a user device to display a message 620, alert 610, or graphical representation 615 associated with the detected indication of pregnancy loss.

In some cases, the user may log symptoms via user input 625. For example, the system may receive user input (e.g., tags) to log symptoms associated with the pregnancy loss, or the like (e.g., flow, cramps, headaches, migraine, pain, etc.). The system may recommend tags to the user based on user history for the user, a group of users, the predicted and/or identified early pregnancy loss, or a combination thereof. In some cases, the system may cause the GUI 600 of the user device to display symptom tags based on a correlation between prior user symptom tags and a timing of the early pregnancy loss.

Application page 605 may also include message 620 that includes insights, recommendations, and the like associated with the predicted and/or identified early pregnancy loss. The server of system may cause the GUI 600 of the user device to display a message 620 associated with the predicted and/or identified early pregnancy loss. The user device may display recommendations and/or information associated with the predicted and/or identified early pregnancy loss via message 620. As noted previously herein, an accurately predicted and/or identified early pregnancy loss may be beneficial to a user's overall health and recovery process.

In some implementations, the system may provide additional insight regarding the user's predicted and/or identified pregnancy loss. For example, the application pages 605 may indicate one or more physiological parameters (e.g., contributing factors) which resulted in the user's predicted and/or identified early pregnancy loss, such as decreased temperature relative to a pregnancy baseline, and the like. In other words, the system may be configured to provide some information or other insights regarding the predicted and/or identified pregnancy loss. Personalized insights may indicate aspects of collected physiological data (e.g., contributing factors within the physiological data) which were used to generate the predicted and/or identified pregnancy loss.

In some implementations, the system may be configured to receive user inputs regarding the identified and/or predicted early pregnancy loss in order to train classifiers (e.g., supervised learning for a machine learning classifier) and improve pregnancy loss determination and/or prediction techniques. For example, the user device may receive user inputs 625, and these user inputs 625 may then be input into the classifier to train the classifier. In some examples, the system may use the detected indication of pregnancy loss to train the system to more accurately and/or precisely predict future pregnancy loss for the user and/or other users. For example, if the user tags a pregnancy loss that the system did not initially predict, the system may detect a pattern indicative of pregnancy loss and apply the pattern to future pregnancies of the user or a group of users.

Upon predicting and/or identifying the early pregnancy loss on application page 605, the GUI 600 may display a calendar view that may indicate a current date that the user is viewing application page 605, a date range including the day when the early pregnancy loss is predicted and/or identified, and a date range including the day when the early pregnancy loss is predicted and/or identified. For example, the date range may encircle the calendar days using a dashed line configuration, the current date may encircle the calendar day, and the day when early pregnancy loss is predicted may be encircled. The calendar view may also include a message including the current calendar day and indication of the day of the user's pregnancy (e.g., that the user is 8 weeks pregnant).

Figure 7:
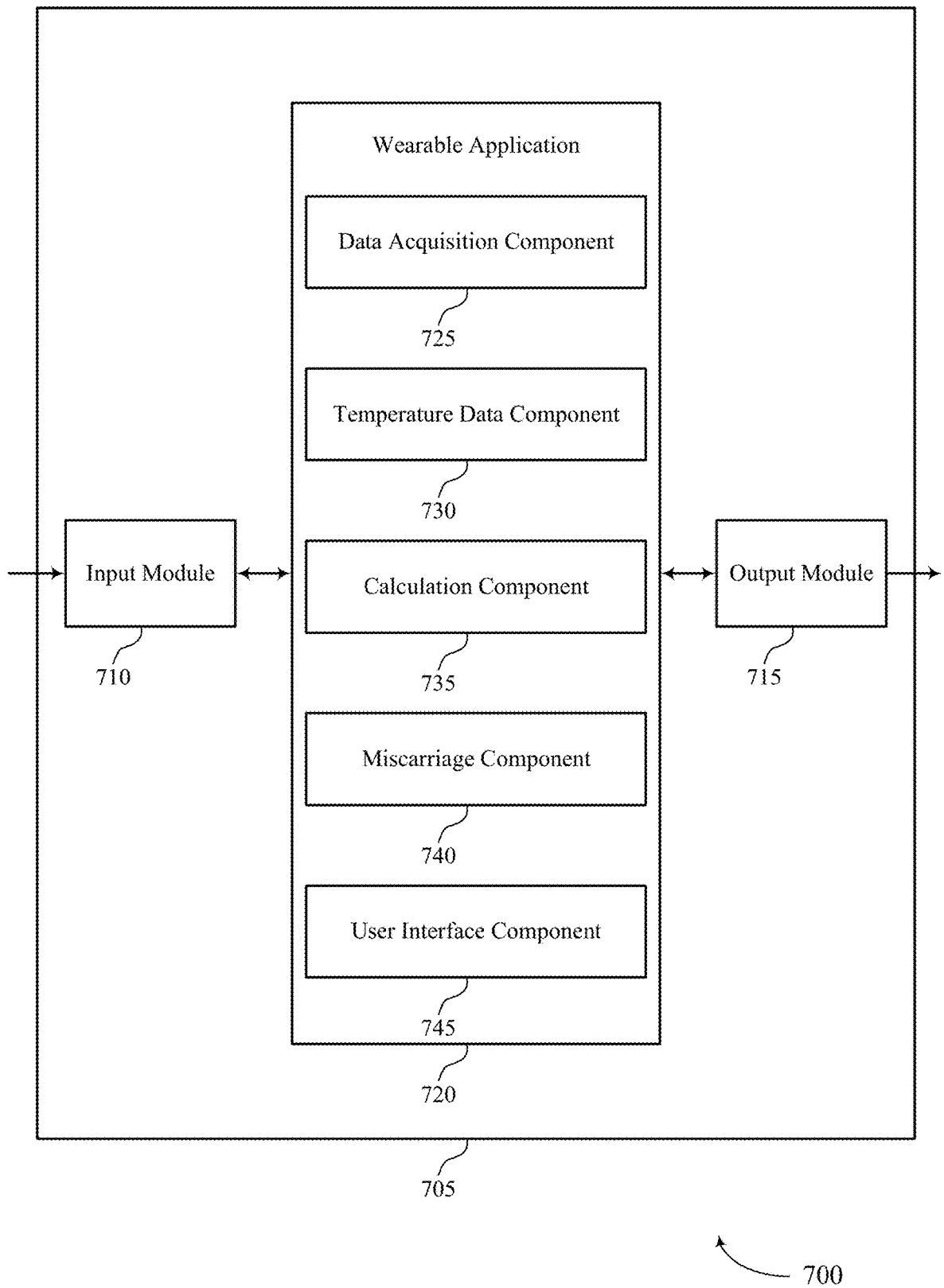
FIG. 7 shows a block diagram of an apparatus that supports miscarriage identification and prediction from wearable-based physiological data in accordance with aspects of the present disclosure.

FIG. 7 shows a block diagram 700 of a device 705 that supports miscarriage identification and prediction from wearable-based physiological data in accordance with aspects of the present disclosure. The device 705 may include an input module 710, an output module 715, and a wearable application 720. The device 705 may also include a processor. Each of these components may be in communication with one another (e.g., via one or more buses).

The input module 710 may provide a means for receiving information such as packets, user data, control information, or any combination thereof associated with various information channels (e.g., control channels, data channels, information channels related to illness detection techniques). Information may be passed on to other components of the device 705. The input module 710 may utilize a single antenna or a set of multiple antennas.

The output module 715 may provide a means for transmitting signals generated by other components of the device 705. For example, the output module 715 may transmit information such as packets, user data, control information, or any combination thereof associated with various information channels (e.g., control channels, data channels, information channels related to illness detection techniques). In some examples, the output module 715 may be co-located with the input module 710 in a transceiver module. The output module 715 may utilize a single antenna or a set of multiple antennas.

For example, the wearable application 720 may include a data acquisition component 725, a temperature data component 730, a calculation component 735, a miscarriage component 740, a user interface component 745, or any combination thereof. In some examples, the wearable application 720, or various components thereof, may be configured to perform various operations (e.g., receiving, monitoring, transmitting) using or otherwise in cooperation with the input module 710, the output module 715, or both. For example, the wearable application 720 may receive information from the input module 710, send information to the output module 715, or be integrated in combination with the input module 710, the output module 715, or both to receive information, transmit information, or perform various other operations as described herein.

The data acquisition component 725 may be configured as or otherwise support a means for receiving, from a wearable device, physiological data associated with a user that is pregnant, the physiological data comprising at least temperature data. The temperature data component 730 may be configured as or otherwise support a means for determining a time series of a plurality of temperature values taken over a plurality of days based at least in part on the received temperature data. The calculation component 735 may be configured as or otherwise support a means for identifying that the plurality of temperature values are lower than a pregnancy baseline of temperature values for the user based at least in part on determining the time series. The miscarriage component 740 may be configured as or otherwise support a means for detecting an indication of an early pregnancy loss of the user based at least in part on identifying that the plurality of temperature values are lower than the pregnancy baseline of temperature values for the user. The user interface component 745 may be configured as or otherwise support a means for generating a message for display on a graphical user interface on a user device that indicates the indication of the early pregnancy loss.

Figure 8:
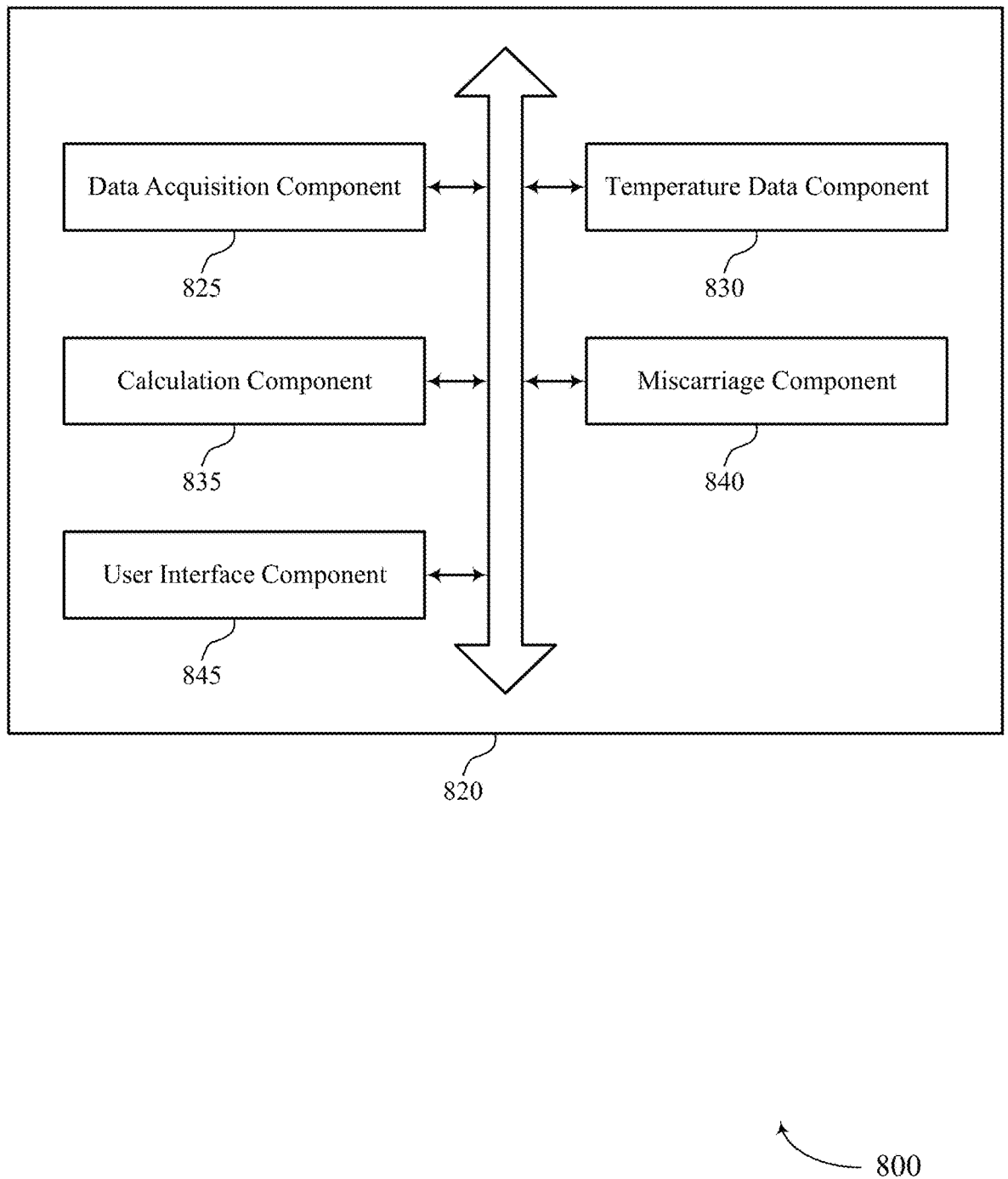
FIG. 8 shows a block diagram of a wearable application that supports miscarriage identification and prediction from wearable-based physiological data in accordance with aspects of the present disclosure.

FIG. 8 shows a block diagram 800 of a wearable application 820 that supports miscarriage identification and prediction from wearable-based physiological data in accordance with aspects of the present disclosure. The wearable application 820 may be an example of aspects of a wearable application or a wearable application 720, or both, as described herein. The wearable application 820, or various components thereof, may be an example of means for performing various aspects of miscarriage identification and prediction from wearable-based physiological data as described herein. For example, the wearable application 820 may include a data acquisition component 825, a temperature data component 830, a calculation component 835, a miscarriage component 840, a user interface component 845, or any combination thereof. Each of these components may communicate, directly or indirectly, with one another (e.g., via one or more buses).

The data acquisition component 825 may be configured as or otherwise support a means for receiving, from a wearable device, physiological data associated with a user that is pregnant, the physiological data comprising at least temperature data. The temperature data component 830 may be configured as or otherwise support a means for determining a time series of a plurality of temperature values taken over a plurality of days based at least in part on the received temperature data. The calculation component 835 may be configured as or otherwise support a means for identifying that the plurality of temperature values are lower than a pregnancy baseline of temperature values for the user based at least in part on determining the time series. The miscarriage component 840 may be configured as or otherwise support a means for detecting an indication of an early pregnancy loss of the user based at least in part on identifying that the plurality of temperature values are lower than the pregnancy baseline of temperature values for the user. The user interface component 845 may be configured as or otherwise support a means for generating a message for display on a graphical user interface on a user device that indicates the indication of the early pregnancy loss.

In some examples, the calculation component 835 may be configured as or otherwise support a means for computing a deviation in the time series of the plurality of temperature values relative to the pregnancy baseline of temperature values for the user based at least in part on determining the time series, wherein the deviation comprises a decrease in the plurality of temperature values from the pregnancy baseline of temperature values for the user, wherein identifying that the plurality of temperature values are lower than the pregnancy baseline of temperature values is based at least in part on computing the deviation.

In some examples, the calculation component 835 may be configured as or otherwise support a means for identifying that one or more positive slopes of the plurality of temperature values are lower than a positive slope for a pregnancy baseline of temperature values for the user based at least in part on determining the time series, wherein identifying that the plurality of temperature values are lower than the pregnancy baseline of temperature values for the user is based at least in part on identifying that the one or more positive slopes are lower than the positive slope for the pregnancy baseline of temperature values for the user.

In some examples, the physiological data further comprises heart rate data, and the data acquisition component 825 may be configured as or otherwise support a means for determining that the received heart rate data exceeds a pregnancy baseline heart rate for the user for at least a portion of the plurality of days, wherein detecting the indication of the early pregnancy loss is based at least in part on determining that the received heart rate data exceeds the pregnancy baseline heart rate for the user.

In some examples, the physiological data further comprises heart rate variability data, and the data acquisition component 825 may be configured as or otherwise support a means for determining that the received heart rate variability data is less than a pregnancy baseline heart rate variability for the user for at least a portion of the plurality of days, wherein detecting the indication of the early pregnancy loss is based at least in part on determining that the received heart rate variability data satisfies the threshold.

In some examples, the physiological data further comprises respiratory rate data, and the data acquisition component 825 may be configured as or otherwise support a means for determining that the received respiratory rate data exceeds a pregnancy baseline respiratory rate for the user for at least a portion of the plurality of days, wherein detecting the indication of the early pregnancy loss is based at least in part on determining that the received respiratory rate data exceeds the pregnancy baseline respiratory rate for the user.

In some examples, the physiological data further comprises sleep data, and the data acquisition component 825 may be configured as or otherwise support a means for determining that a quantity of detected sleep disturbances from the received sleep data exceeds a pregnancy baseline sleep disturbance threshold for the user for at least a portion of the plurality of days, wherein detecting the indication of the early pregnancy loss is based at least in part on determining that the quantity of detected sleep disturbances exceeds the pregnancy baseline sleep disturbance threshold for the user.

In some examples, the miscarriage component 840 may be configured as or otherwise support a means for identifying a presence of a menstrual cycle within a time period after pregnancy based at least in part on determining the time series, wherein detecting the indication of the early pregnancy loss is based at least in part on identifying the presence of the menstrual cycle.

In some examples, the user interface component 845 may be configured as or otherwise support a means for receiving a confirmation of a menstrual cycle within a time period after pregnancy, a confirmation of a pregnancy loss, or both, wherein detecting the indication of the early pregnancy loss is based at least in part on receiving the confirmation.

In some examples, the temperature data component 830 may be configured as or otherwise support a means for determining each temperature value of the plurality of temperature values based at least in part on receiving the temperature data, wherein the temperature data comprises continuous nighttime temperature data.

In some examples, the miscarriage component 840 may be configured as or otherwise support a means for estimating a likelihood of future early pregnancy loss, a likelihood that the user will experience the early pregnancy loss, or both, based at least in part on identifying that the plurality of temperature values are lower than the pregnancy baseline of temperature values for the user, wherein detecting the indication of the early pregnancy loss is based at least in part on the estimation.

In some examples, the calculation component 835 may be configured as or otherwise support a means for updating a readiness score associated with the user, an activity score associated with the user, a sleep score associated with the user, or a combination thereof, based at least in part on detecting the indication of the early pregnancy loss.

In some examples, the user interface component 845 may be configured as or otherwise support a means for transmitting the message that indicates the indication of the early pregnancy loss to the user device, wherein the user device is associated with a clinician, the user, or both.

In some examples, the user interface component 845 may be configured as or otherwise support a means for causing a graphical user interface of a user device associated with the user to display early pregnancy loss symptom tags based at least in part on detecting the indication of the early pregnancy loss.

In some examples, the user interface component 845 may be configured as or otherwise support a means for causing a graphical user interface of a user device associated with the user to display a message associated with the indication of the early pregnancy loss.

In some examples, the message further comprises a time interval during which the early pregnancy loss occurred, a time interval during which the early pregnancy loss is predicted to occur, a request to input symptoms associated with the early pregnancy loss, educational content associated with the early pregnancy loss, an adjusted set of sleep targets, an adjusted set of activity targets, recommendations to improve symptoms associated with the early pregnancy loss, or a combination thereof.

In some examples, the calculation component 835 may be configured as or otherwise support a means for inputting the physiological data into a machine learning classifier, wherein detecting the indication of the early pregnancy loss is based at least in part on inputting the physiological data into the machine learning classifier.

In some examples, the wearable device comprises a wearable ring device.

In some examples, the wearable device collects the physiological data from the user based on arterial blood flow.

Figure 9:
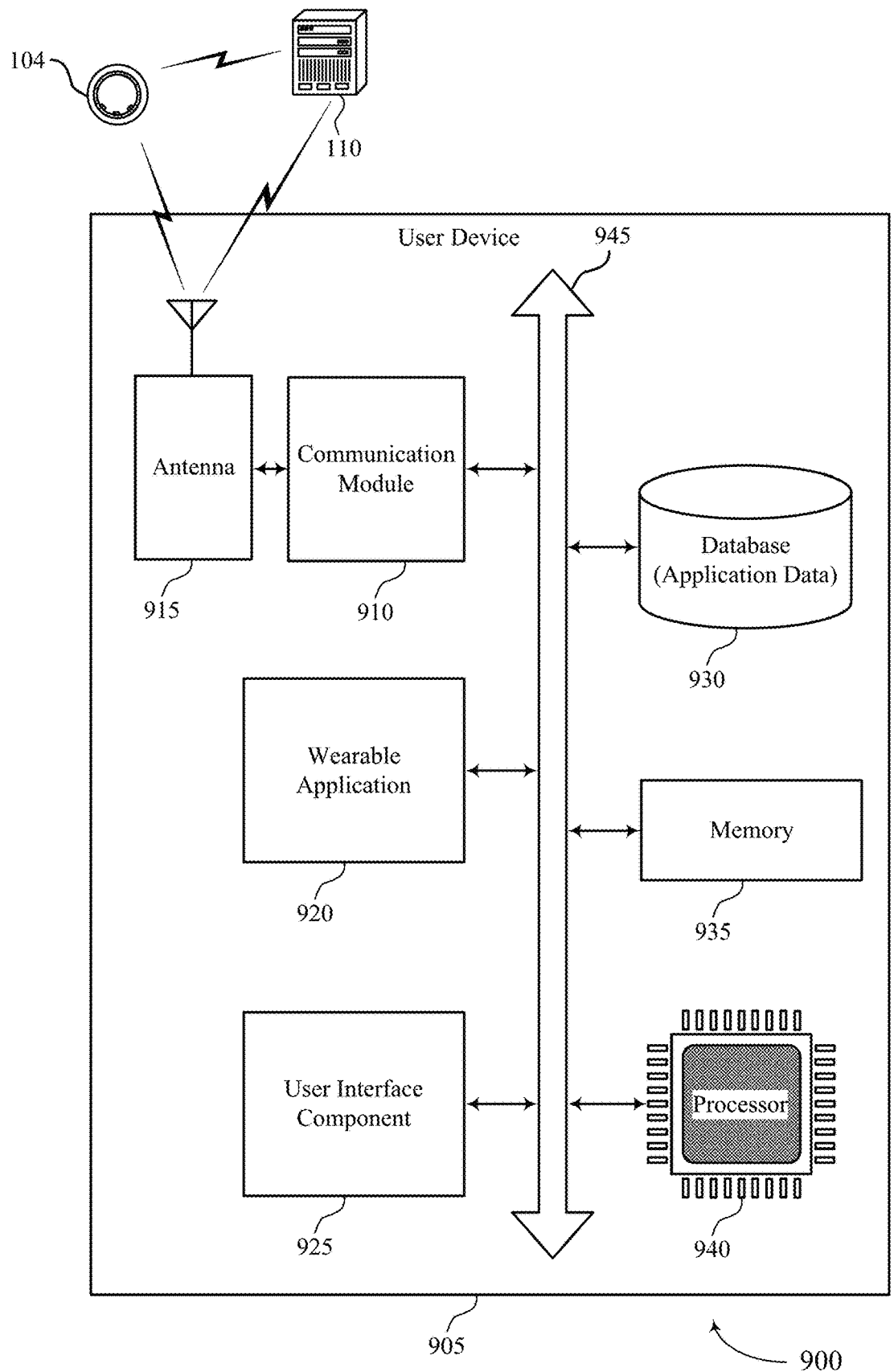
FIG. 9 shows a diagram of a system including a device that supports miscarriage identification and prediction from wearable-based physiological data in accordance with aspects of the present disclosure.

FIG. 9 shows a diagram of a system 900 including a device 905 that supports miscarriage identification and prediction from wearable-based physiological data in accordance with aspects of the present disclosure. The device 905 may be an example of or include the components of a device 705 as described herein. The device 905 may include an example of a user device 106, as described previously herein. The device 905 may include components for bi-directional communications including components for transmitting and receiving communications with a wearable device 104 and a server 110, such as a wearable application 920, a communication module 910, an antenna 915, a user interface component 925, a database (application data) 930, a memory 935, and a processor 940. These components may be in electronic communication or otherwise coupled (e.g., operatively, communicatively, functionally, electronically, electrically) via one or more buses (e.g., a bus 945).

The communication module 910 may manage input and output signals for the device 905 via the antenna 915. The communication module 910 may include an example of the communication module 220-*b* of the user device 106 shown and described in FIG. 2. In this regard, the communication module 910 may manage communications with the ring 104 and the server 110, as illustrated in FIG. 2. The communication module 910 may also manage peripherals not integrated into the device 905. In some cases, the communication module 910 may represent a physical connection or port to an external peripheral. In some cases, the communication module 910 may utilize an operating system such as iOS®, ANDROID®, MS-DOS®, MS-WINDOWS®, OS/2®, UNIX®, LINUX®, or another known operating system. In other cases, the communication module 910 may represent or interact with a wearable device (e.g., ring 104), modem, a keyboard, a mouse, a touchscreen, or a similar device. In some cases, the communication module 910 may be implemented as part of the processor 940. In some examples, a user may interact with the device 905 via the communication module 910, user interface component 925, or via hardware components controlled by the communication module 910.

In some cases, the device 905 may include a single antenna 915. However, in some other cases, the device 905 may have more than one antenna 915, which may be capable of concurrently transmitting or receiving multiple wireless transmissions. The communication module 910 may communicate bi-directionally, via the one or more antennas 915, wired, or wireless links as described herein. For example, the communication module 910 may represent a wireless transceiver and may communicate bi-directionally with another wireless transceiver. The communication module 910 may also include a modem to modulate the packets, to provide the modulated packets to one or more antennas 915 for transmission, and to demodulate packets received from the one or more antennas 915.

The user interface component 925 may manage data storage and processing in a database 930. In some cases, a user may interact with the user interface component 925. In other cases, the user interface component 925 may operate automatically without user interaction. The database 930 may be an example of a single database, a distributed database, multiple distributed databases, a data store, a data lake, or an emergency backup database.

The memory 935 may include RAM and ROM. The memory 935 may store computer-readable, computer-executable software including instructions that, when executed, cause the processor 940 to perform various functions described herein. In some cases, the memory 935 may contain, among other things, a BIOS which may control basic hardware or software operation such as the interaction with peripheral components or devices.

The processor 940 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 940 may be configured to operate a memory array using a memory controller. In other cases, a memory controller may be integrated into the processor 940. The processor 940 may be configured to execute computer-readable instructions stored in a memory 935 to perform various functions (e.g., functions or tasks supporting a method and system for sleep staging algorithms).

For example, the wearable application 920 may be configured as or otherwise support a means for receiving, from a wearable device, physiological data associated with a user that is pregnant, the physiological data comprising at least temperature data. The wearable application 920 may be configured as or otherwise support a means for determining a time series of a plurality of temperature values taken over a plurality of days based at least in part on the received temperature data. The wearable application 920 may be configured as or otherwise support a means for identifying that the plurality of temperature values are lower than a pregnancy baseline of temperature values for the user based at least in part on determining the time series. The wearable application 920 may be configured as or otherwise support a means for detecting an indication of an early pregnancy loss of the user based at least in part on identifying that the plurality of temperature values are lower than the pregnancy baseline of temperature values for the user. The wearable application 920 may be configured as or otherwise support a means for generating a message for display on a graphical user interface on a user device that indicates the indication of the early pregnancy loss.

By including or configuring the wearable application 920 in accordance with examples as described herein, the device 905 may support techniques for improved communication reliability, reduced latency, improved user experience related to reduced processing, reduced power consumption, more efficient utilization of communication resources, improved coordination between devices, longer battery life, improved utilization of processing capability.

The wearable application 920 may include an application (e.g., "app"), program, software, or other component which is configured to facilitate communications with a ring 104, server 110, other user devices 106, and the like. For example, the wearable application 920 may include an application executable on a user device 106 which is configured to receive data (e.g., physiological data) from a ring 104, perform processing operations on the received data, transmit and receive data with the servers 110, and cause presentation of data to a user 102.

Figure 10:
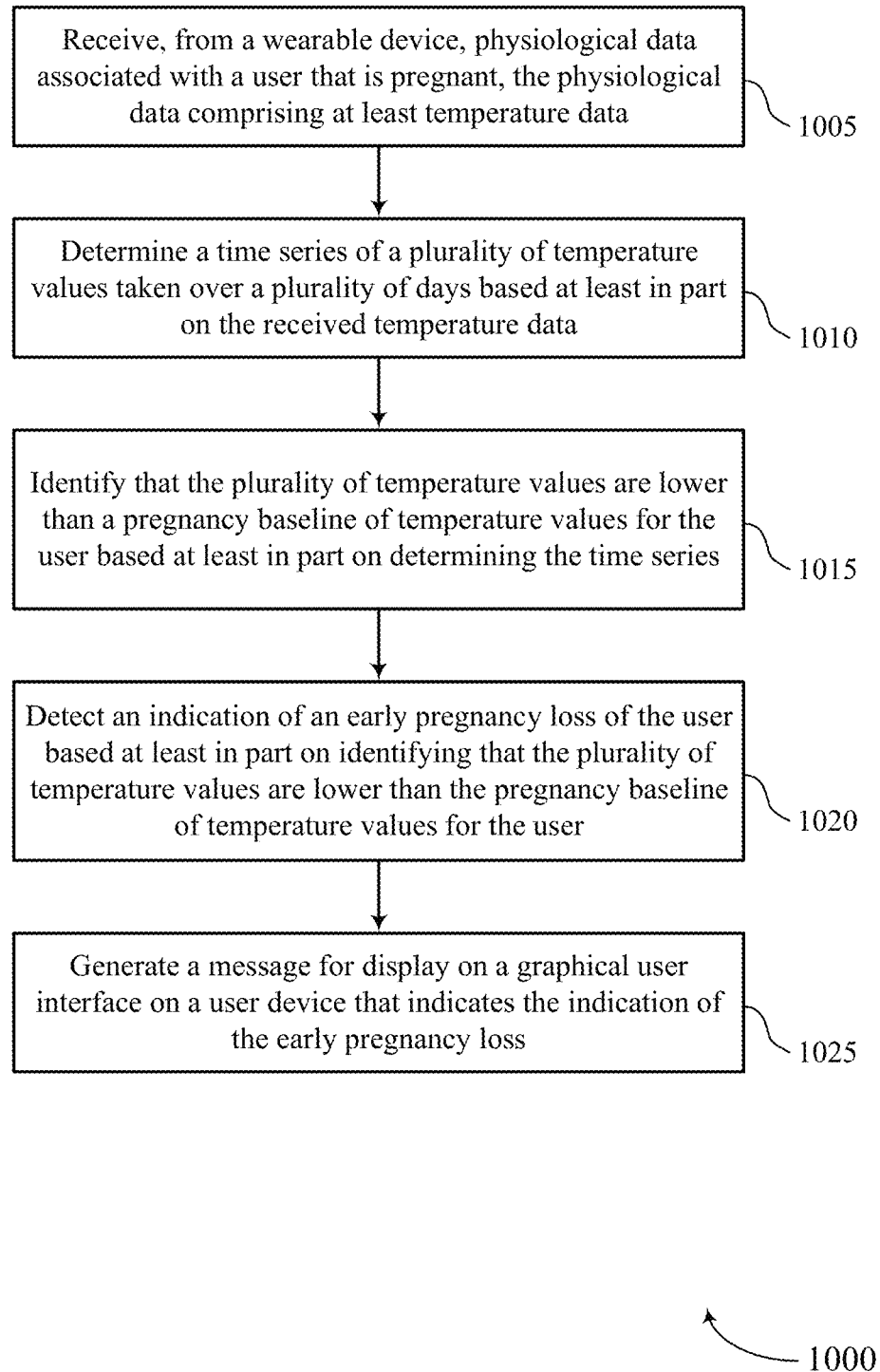
FIGS. 10 through 12 show flowcharts illustrating methods that support miscarriage identification and prediction from wearable-based physiological data in accordance with aspects of the present disclosure.

FIG. 10 shows a flowchart illustrating a method 1000 that supports miscarriage identification and prediction from wearable-based physiological data in accordance with aspects of the present disclosure. The operations of the method 1000 may be implemented by a user device or its components as described herein. For example, the operations of the method 1000 may be performed by a user device as described with reference to FIGS. 1 through 9. In some examples, a user device may execute a set of instructions to control the functional elements of the user device to perform the described functions. Additionally, or alternatively, the user device may perform aspects of the described functions using special-purpose hardware.

At 1005, the method may include receiving, from a wearable device, physiological data associated with a user that is pregnant, the physiological data comprising at least temperature data. The operations of 1005 may be performed in accordance with examples as disclosed herein. In some examples, aspects of the operations of 1005 may be performed by a data acquisition component 825 as described with reference to FIG. 8.

At 1010, the method may include determining a time series of a plurality of temperature values taken over a plurality of days based at least in part on the received temperature data. The operations of 1010 may be performed in accordance with examples as disclosed herein. In some examples, aspects of the operations of 1010 may be performed by a temperature data component 830 as described with reference to FIG. 8.

At 1015, the method may include identifying that the plurality of temperature values are lower than a pregnancy baseline of temperature values for the user based at least in part on determining the time series. The operations of 1015 may be performed in accordance with examples as disclosed herein. In some examples, aspects of the operations of 1015 may be performed by a calculation component 835 as described with reference to FIG. 8.

At 1020, the method may include detecting an indication of an early pregnancy loss of the user based at least in part on identifying that the plurality of temperature values are lower than the pregnancy baseline of temperature values for the user. The operations of 1020 may be performed in accordance with examples as disclosed herein. In some examples, aspects of the operations of 1020 may be performed by a miscarriage component 840 as described with reference to FIG. 8.

At 1025, the method may include generating a message for display on a graphical user interface on a user device that indicates the indication of the early pregnancy loss. The operations of 1025 may be performed in accordance with examples as disclosed herein. In some examples, aspects of the operations of 1025 may be performed by a user interface component 845 as described with reference to FIG. 8.

Figure 11:
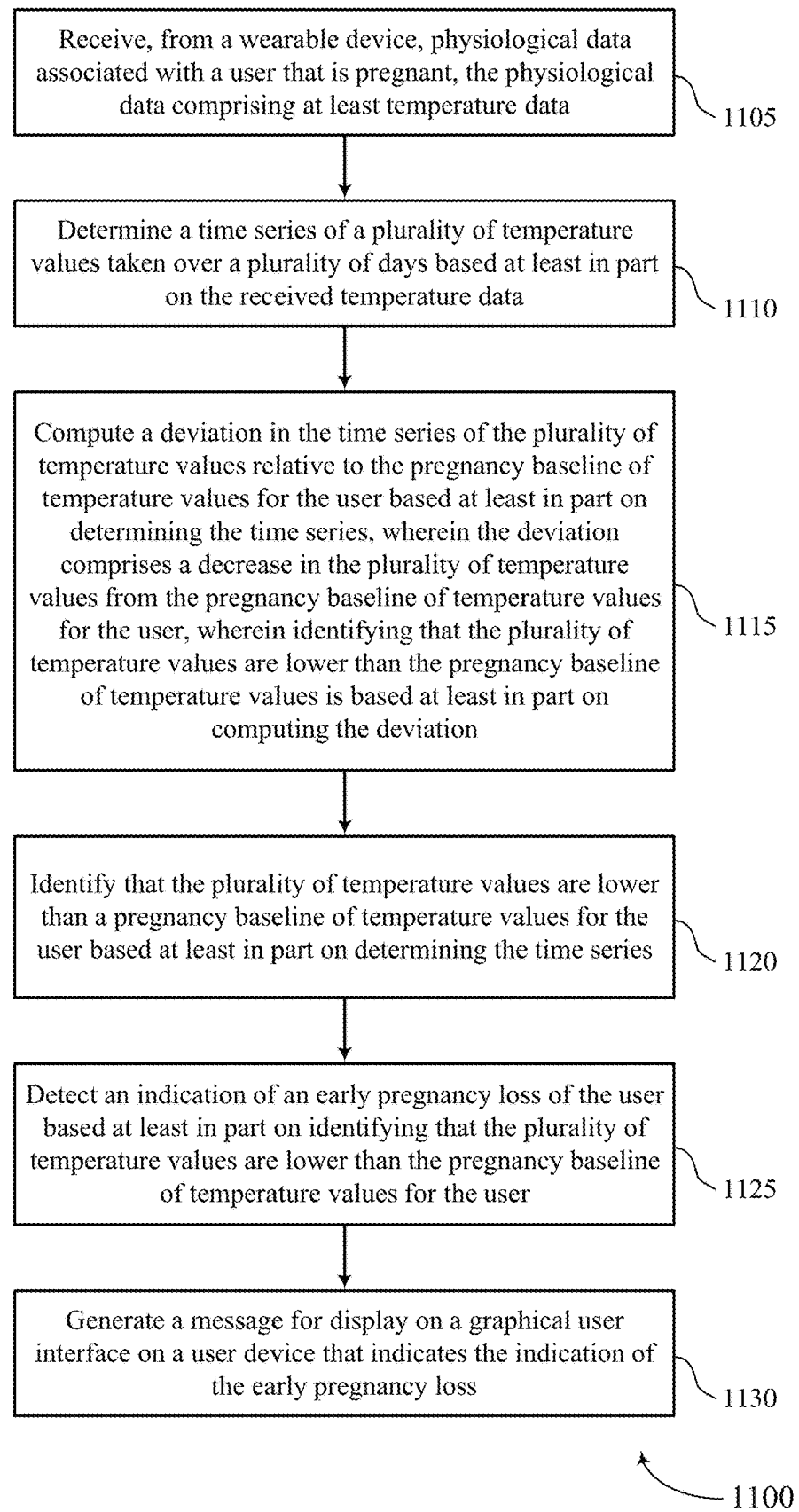

FIG. 11 shows a flowchart illustrating a method 1100 that supports miscarriage identification and prediction from wearable-based physiological data in accordance with aspects of the present disclosure. The operations of the method 1100 may be implemented by a user device or its components as described herein. For example, the operations of the method 1100 may be performed by a user device as described with reference to FIGS. 1 through 9. In some examples, a user device may execute a set of instructions to control the functional elements of the user device to perform the described functions. Additionally, or alternatively, the user device may perform aspects of the described functions using special-purpose hardware.

At 1105, the method may include receiving, from a wearable device, physiological data associated with a user that is pregnant, the physiological data comprising at least temperature data. The operations of 1105 may be performed in accordance with examples as disclosed herein. In some examples, aspects of the operations of 1105 may be performed by a data acquisition component 825 as described with reference to FIG. 8.

At 1110, the method may include determining a time series of a plurality of temperature values taken over a plurality of days based at least in part on the received temperature data. The operations of 1110 may be performed in accordance with examples as disclosed herein. In some examples, aspects of the operations of 1110 may be performed by a temperature data component 830 as described with reference to FIG. 8.

At 1115, the method may include computing a deviation in the time series of the plurality of temperature values relative to the pregnancy baseline of temperature values for the user based at least in part on determining the time series, wherein the deviation comprises a decrease in the plurality of temperature values from the pregnancy baseline of temperature values for the user, wherein identifying that the plurality of temperature values are lower than the pregnancy baseline of temperature values is based at least in part on computing the deviation. The operations of 1115 may be performed in accordance with examples as disclosed herein. In some examples, aspects of the operations of 1115 may be performed by a calculation component 835 as described with reference to FIG. 8.

At 1120, the method may include identifying that the plurality of temperature values are lower than a pregnancy baseline of temperature values for the user based at least in part on determining the time series. The operations of 1120 may be performed in accordance with examples as disclosed herein. In some examples, aspects of the operations of 1120 may be performed by a calculation component 835 as described with reference to FIG. 8.

At 1125, the method may include detecting an indication of an early pregnancy loss of the user based at least in part on identifying that the plurality of temperature values are lower than the pregnancy baseline of temperature values for the user. The operations of 1125 may be performed in accordance with examples as disclosed herein. In some examples, aspects of the operations of 1125 may be performed by a miscarriage component 840 as described with reference to FIG. 8.

At 1130, the method may include generating a message for display on a graphical user interface on a user device that indicates the indication of the early pregnancy loss. The operations of 1130 may be performed in accordance with examples as disclosed herein. In some examples, aspects of the operations of 1130 may be performed by a user interface component 845 as described with reference to FIG. 8.

Figure 12:
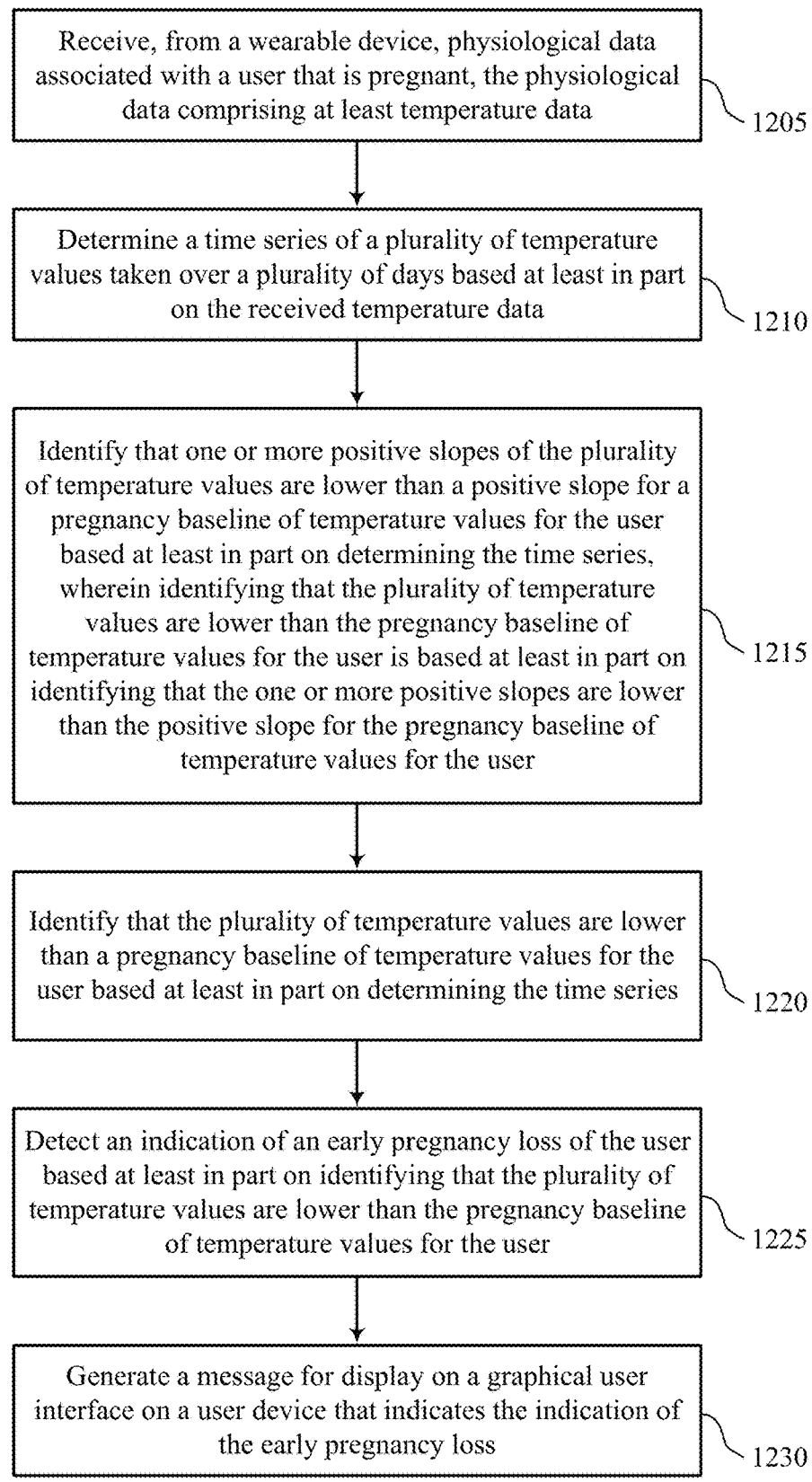

FIG. 12 shows a flowchart illustrating a method 1200 that supports miscarriage identification and prediction from wearable-based physiological data in accordance with aspects of the present disclosure. The operations of the method 1200 may be implemented by a user device or its components as described herein. For example, the operations of the method 1200 may be performed by a user device as described with reference to FIGS. 1 through 9. In some examples, a user device may execute a set of instructions to control the functional elements of the user device to perform the described functions. Additionally, or alternatively, the user device may perform aspects of the described functions using special-purpose hardware.

At 1205, the method may include receiving, from a wearable device, physiological data associated with a user that is pregnant, the physiological data comprising at least temperature data. The operations of 1205 may be performed in accordance with examples as disclosed herein. In some examples, aspects of the operations of 1205 may be performed by a data acquisition component 825 as described with reference to FIG. 8.

At 1210, the method may include determining a time series of a plurality of temperature values taken over a plurality of days based at least in part on the received temperature data. The operations of 1210 may be performed in accordance with examples as disclosed herein. In some examples, aspects of the operations of 1210 may be performed by a temperature data component 830 as described with reference to FIG. 8.

At 1215, the method may include identifying that one or more positive slopes of the plurality of temperature values are lower than a positive slope for a pregnancy baseline of temperature values for the user based at least in part on determining the time series, wherein identifying that the plurality of temperature values are lower than the pregnancy baseline of temperature values for the user is based at least in part on identifying that the one or more positive slopes are lower than the positive slope for the pregnancy baseline of temperature values for the user. The operations of 1215 may be performed in accordance with examples as disclosed herein. In some examples, aspects of the operations of 1215 may be performed by a calculation component 835 as described with reference to FIG. 8.

At 1220, the method may include identifying that the plurality of temperature values are lower than a pregnancy baseline of temperature values for the user based at least in part on determining the time series. The operations of 1220 may be performed in accordance with examples as disclosed herein. In some examples, aspects of the operations of 1220 may be performed by a calculation component 835 as described with reference to FIG. 8.

At 1225, the method may include detecting an indication of an early pregnancy loss of the user based at least in part on identifying that the plurality of temperature values are lower than the pregnancy baseline of temperature values for the user. The operations of 1225 may be performed in accordance with examples as disclosed herein. In some examples, aspects of the operations of 1225 may be performed by a miscarriage component 840 as described with reference to FIG. 8.

At 1230, the method may include generating a message for display on a graphical user interface on a user device that indicates the indication of the early pregnancy loss. The operations of 1230 may be performed in accordance with examples as disclosed herein. In some examples, aspects of the operations of 1230 may be performed by a user interface component 845 as described with reference to FIG. 8.

It should be noted that the methods described above describe possible implementations, and that the operations and the steps may be rearranged or otherwise modified and that other implementations are possible. Furthermore, aspects from two or more of the methods may be combined.

A method is described. The method may include receiving, from a wearable device, physiological data associated with a user that is pregnant, the physiological data comprising at least temperature data, determining a time series of a plurality of temperature values taken over a plurality of days based at least in part on the received temperature data, identifying that the plurality of temperature values are lower than a pregnancy baseline of temperature values for the user based at least in part on determining the time series, detecting an indication of an early pregnancy loss of the user based at least in part on identifying that the plurality of temperature values are lower than the pregnancy baseline of temperature values for the user, and generating a message for display on a graphical user interface on a user device that indicates the indication of the early pregnancy loss.

An apparatus is described. The apparatus may include a processor, memory coupled with the processor, and instructions stored in the memory. The instructions may be executable by the processor to cause the apparatus to receive, from a wearable device, physiological data associated with a user that is pregnant, the physiological data comprising at least temperature data, determine a time series of a plurality of temperature values taken over a plurality of days based at least in part on the received temperature data, identify that the plurality of temperature values are lower than a pregnancy baseline of temperature values for the user based at least in part on determining the time series, detect an indication of an early pregnancy loss of the user based at least in part on identifying that the plurality of temperature values are lower than the pregnancy baseline of temperature values for the user, and generate a message for display on a graphical user interface on a user device that indicates the indication of the early pregnancy loss.

Another apparatus is described. The apparatus may include means for receiving, from a wearable device, physiological data associated with a user that is pregnant, the physiological data comprising at least temperature data, means for determining a time series of a plurality of temperature values taken over a plurality of days based at least in part on the received temperature data, means for identifying that the plurality of temperature values are lower than a pregnancy baseline of temperature values for the user based at least in part on determining the time series, means for detecting an indication of an early pregnancy loss of the user based at least in part on identifying that the plurality of temperature values are lower than the pregnancy baseline of temperature values for the user, and means for generating a message for display on a graphical user interface on a user device that indicates the indication of the early pregnancy loss.

A non-transitory computer-readable medium storing code is described. The code may include instructions executable by a processor to receive, from a wearable device, physiological data associated with a user that is pregnant, the physiological data comprising at least temperature data, determine a time series of a plurality of temperature values taken over a plurality of days based at least in part on the received temperature data, identify that the plurality of temperature values are lower than a pregnancy baseline of temperature values for the user based at least in part on determining the time series, detect an indication of an early pregnancy loss of the user based at least in part on identifying that the plurality of temperature values are lower than the pregnancy baseline of temperature values for the user, and generate a message for display on a graphical user interface on a user device that indicates the indication of the early pregnancy loss.

Some examples of the method, apparatuses, and non-transitory computer-readable medium described herein may further include operations, features, means, or instructions for computing a deviation in the time series of the plurality of temperature values relative to the pregnancy baseline of temperature values for the user based at least in part on determining the time series, wherein the deviation comprises a decrease in the plurality of temperature values from the pregnancy baseline of temperature values for the user, wherein identifying that the plurality of temperature values may be lower than the pregnancy baseline of temperature values may be based at least in part on computing the deviation.

Some examples of the method, apparatuses, and non-transitory computer-readable medium described herein may further include operations, features, means, or instructions for identifying that one or more positive slopes of the plurality of temperature values may be lower than a positive slope for a pregnancy baseline of temperature values for the user based at least in part on determining the time series, wherein identifying that the plurality of temperature values may be lower than the pregnancy baseline of temperature values for the user may be based at least in part on identifying that the one or more positive slopes may be lower than the positive slope for the pregnancy baseline of temperature values for the user.

In some examples of the method, apparatuses, and non-transitory computer-readable medium described herein, the physiological data further comprises heart rate data and the method, apparatuses, and non-transitory computer-readable medium may include further operations, features, means, or instructions for determining that the received heart rate data exceeds a pregnancy baseline heart rate for the user for at least a portion of the plurality of days, wherein detecting the indication of the early pregnancy loss may be based at least in part on determining that the received heart rate data exceeds the pregnancy baseline heart rate for the user.

In some examples of the method, apparatuses, and non-transitory computer-readable medium described herein, the physiological data further comprises heart rate variability data and the method, apparatuses, and non-transitory computer-readable medium may include further operations, features, means, or instructions for determining that the received heart rate variability data may be less than a pregnancy baseline heart rate variability for the user for at least a portion of the plurality of days, wherein detecting the indication of the early pregnancy loss may be based at least in part on determining that the received heart rate variability data satisfies the threshold.

In some examples of the method, apparatuses, and non-transitory computer-readable medium described herein, the physiological data further comprises respiratory rate data and the method, apparatuses, and non-transitory computer-readable medium may include further operations, features, means, or instructions for determining that the received respiratory rate data exceeds a pregnancy baseline respiratory rate for the user for at least a portion of the plurality of days, wherein detecting the indication of the early pregnancy loss may be based at least in part on determining that the received respiratory rate data exceeds the pregnancy baseline respiratory rate for the user.

In some examples of the method, apparatuses, and non-transitory computer-readable medium described herein, the physiological data further comprises sleep data and the method, apparatuses, and non-transitory computer-readable medium may include further operations, features, means, or instructions for determining that a quantity of detected sleep disturbances from the received sleep data exceeds a pregnancy baseline sleep disturbance threshold for the user for at least a portion of the plurality of days, wherein detecting the indication of the early pregnancy loss may be based at least in part on determining that the quantity of detected sleep disturbances exceeds the pregnancy baseline sleep disturbance threshold for the user.

Some examples of the method, apparatuses, and non-transitory computer-readable medium described herein may further include operations, features, means, or instructions for identifying a presence of a menstrual cycle within a time period after pregnancy based at least in part on determining the time series, wherein detecting the indication of the early pregnancy loss may be based at least in part on identifying the presence of the menstrual cycle.

Some examples of the method, apparatuses, and non-transitory computer-readable medium described herein may further include operations, features, means, or instructions for receiving a confirmation of a menstrual cycle within a time period after pregnancy, a confirmation of a pregnancy loss, or both, wherein detecting the indication of the early pregnancy loss may be based at least in part on receiving the confirmation.

Some examples of the method, apparatuses, and non-transitory computer-readable medium described herein may further include operations, features, means, or instructions for determining each temperature value of the plurality of temperature values based at least in part on receiving the temperature data, wherein the temperature data comprises continuous nighttime temperature data.

Some examples of the method, apparatuses, and non-transitory computer-readable medium described herein may further include operations, features, means, or instructions for estimating a likelihood of future early pregnancy loss, a likelihood that the user will experience the early pregnancy loss, or both, based at least in part on identifying that the plurality of temperature values may be lower than the pregnancy baseline of temperature values for the user, wherein detecting the indication of the early pregnancy loss may be based at least in part on the estimation.

Some examples of the method, apparatuses, and non-transitory computer-readable medium described herein may further include operations, features, means, or instructions for updating a readiness score associated with the user, an activity score associated with the user, a sleep score associated with the user, or a combination thereof, based at least in part on detecting the indication of the early pregnancy loss.

Some examples of the method, apparatuses, and non-transitory computer-readable medium described herein may further include operations, features, means, or instructions for transmitting the message that indicates the indication of the early pregnancy loss to the user device, wherein the user device may be associated with a clinician, the user, or both.

Some examples of the method, apparatuses, and non-transitory computer-readable medium described herein may further include operations, features, means, or instructions for causing a graphical user interface of a user device associated with the user to display early pregnancy loss symptom tags based at least in part on detecting the indication of the early pregnancy loss.

Some examples of the method, apparatuses, and non-transitory computer-readable medium described herein may further include operations, features, means, or instructions for causing a graphical user interface of a user device associated with the user to display a message associated with the indication of the early pregnancy loss.

In some examples of the method, apparatuses, and non-transitory computer-readable medium described herein, the message further comprises a time interval during which the early pregnancy loss occurred, a time interval during which the early pregnancy loss may be predicted to occur, a request to input symptoms associated with the early pregnancy loss, educational content associated with the early pregnancy loss, an adjusted set of sleep targets, an adjusted set of activity targets, recommendations to improve symptoms associated with the early pregnancy loss, or a combination thereof.

Some examples of the method, apparatuses, and non-transitory computer-readable medium described herein may further include operations, features, means, or instructions for inputting the physiological data into a machine learning classifier, wherein detecting the indication of the early pregnancy loss may be based at least in part on inputting the physiological data into the machine learning classifier.

In some examples of the method, apparatuses, and non-transitory computer-readable medium described herein, the wearable device comprises a wearable ring device.

In some examples of the method, apparatuses, and non-transitory computer-readable medium described herein, the wearable device collects the physiological data from the user based on arterial blood flow.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method comprising:
   acquiring, via one or more temperature sensors of a wearable ring device configured to be worn by a user that is pregnant, physiological data associated with the user;
   receiving, via a transceiver of a user device and from the wearable ring device, the physiological data associated with the user, the physiological data comprising at least temperature data;
   determining a time series of a plurality of temperature values taken over a plurality of days based at least in part on the received temperature data;
   identifying that the plurality of temperature values are lower than a pregnancy baseline of temperature values for the user based at least in part on determining the time series;

identifying that one or more positive slopes of the plurality of temperature values are lower than a positive slope of the pregnancy baseline of temperature values for the user based at least in part on determining the time series;

detecting an indication of an early pregnancy loss of the user based at least in part on identifying that the plurality of temperature values are lower than the pregnancy baseline of temperature values for the user and based at least in part on identifying that the one or more positive slopes of the plurality of temperature values are lower than the positive slope for the pregnancy baseline of temperature values for the user; and generating a message for display on a graphical user interface of the user device that indicates the indication of the early pregnancy loss.

2. The method of claim 1, further comprising:
computing a deviation in the time series of the plurality of temperature values relative to the pregnancy baseline of temperature values for the user based at least in part on determining the time series, wherein the deviation comprises a decrease in the plurality of temperature values from the pregnancy baseline of temperature values for the user, wherein identifying that the plurality of temperature values are lower than the pregnancy baseline of temperature values is based at least in part on computing the deviation.

3. The method of claim 1, wherein the physiological data further comprises heart rate data, the method further comprising:
acquiring the heart rate data via one or more light-emitting components and one or more light-receiving components of the wearable ring device; and
determining that the received heart rate data exceeds a pregnancy baseline heart rate for the user for at least a portion of the plurality of days, wherein detecting the indication of the early pregnancy loss is based at least in part on determining that the received heart rate data exceeds the pregnancy baseline heart rate for the user.

4. The method of claim 1, wherein the physiological data further comprises heart rate variability data, the method further comprising:
acquiring the heart rate variability data via one or more light-emitting components and one or more light-receiving components of the wearable ring device; and
determining that the received heart rate variability data is less than a pregnancy baseline heart rate variability for the user for at least a portion of the plurality of days, wherein detecting the indication of the early pregnancy loss is based at least in part on determining that the received heart rate variability data is less than the pregnancy baseline heart rate variability.

5. The method of claim 1, wherein the physiological data further comprises respiratory rate data, the method further comprising:
acquiring the respiratory rate data via one or more light-emitting components and one or more light-receiving components of the wearable ring device; and
determining that the received respiratory rate data exceeds a pregnancy baseline respiratory rate for the user for at least a portion of the plurality of days, wherein detecting the indication of the early pregnancy loss is based at least in part on determining that the received respiratory rate data exceeds the pregnancy baseline respiratory rate for the user.

6. The method of claim 1, wherein the physiological data further comprises sleep data, the method further comprising:
acquiring the sleep data via one or more light-emitting components and one or more light-receiving components of the wearable ring device; and
determining that a quantity of detected sleep disturbances from the received sleep data exceeds a pregnancy baseline sleep disturbance threshold for the user for at least a portion of the plurality of days, wherein detecting the indication of the early pregnancy loss is based at least in part on determining that the quantity of detected sleep disturbances exceeds the pregnancy baseline sleep disturbance threshold for the user.

7. The method of claim 1, further comprising:
identifying a presence of a menstrual cycle within a time period after pregnancy based at least in part on determining the time series, wherein detecting the indication of the early pregnancy loss is based at least in part on identifying the presence of the menstrual cycle.

8. The method of claim 1, further comprising:
receiving a confirmation of a menstrual cycle within a time period after pregnancy, a confirmation of a pregnancy loss, or both, wherein detecting the indication of the early pregnancy loss is based at least in part on receiving the confirmation.

9. The method of claim 1, further comprising:
determining each temperature value of the plurality of temperature values based at least in part on receiving the temperature data, wherein the temperature data comprises continuous nighttime temperature data.

10. The method of claim 1, further comprising:
estimating a likelihood of future early pregnancy loss, a likelihood that the user will experience the early pregnancy loss, or both, based at least in part on identifying that the plurality of temperature values are lower than the pregnancy baseline of temperature values for the user, wherein detecting the indication of the early pregnancy loss is based at least in part on the estimation.

11. The method of claim 1, further comprising:
identifying a false positive for identifying the indication of the early pregnancy loss based on a physiological measurement or a combination of physiological measurements.

12. The method of claim 1, further comprising:
transmitting the message that indicates the indication of the early pregnancy loss to the user device, wherein the user device is associated with a clinician, the user, or both.

13. The method of claim 1, further comprising: causing the graphical user interface of the user device associated with the user to display early pregnancy loss symptom tags based at least in part on detecting the indication of the early pregnancy loss.

14. The method of claim 1, further comprising: causing the graphical user interface of the user device associated with the user to display a message associated with the indication of the early pregnancy loss.

15. The method of claim 14, wherein the message further comprises a time interval during which the early pregnancy loss occurred, a time interval during which the early pregnancy loss is predicted to occur, a request to input symptoms associated with the early pregnancy loss, educational content associated with the early pregnancy loss, an adjusted set of sleep targets, an adjusted set of activity targets, recommendations to improve symptoms associated with the early pregnancy loss, or a combination thereof.

16. The method of claim 1, further comprising:
inputting the physiological data into a machine learning classifier, wherein detecting the indication of the early pregnancy loss is based at least in part on inputting the physiological data into the machine learning classifier.

17. An apparatus, comprising:
a processor;
memory coupled with the processor, and
instructions stored in the memory and executable by the processor to cause the apparatus to:
acquire, via one or more temperature sensors of a wearable ring device configured to be worn by a user that is pregnant, physiological data associated with the user;
receive, via a transceiver of a user device and from the wearable ring device, the physiological data associated with the user, the physiological data comprising at least temperature data;
determine a time series of a plurality of temperature values taken over a plurality of days based at least in part on the received temperature data;
identify that the plurality of temperature values are lower than a pregnancy baseline of temperature values for the user based at least in part on determining the time series;
identify that one or more positive slopes of the plurality of temperature values are lower than a positive slope of the pregnancy baseline of temperature values for the user based at least in part on determining the time series;
detect an indication of an early pregnancy loss of the user based at least in part on identifying that the plurality of temperature values are lower than the pregnancy baseline of temperature values for the user and based at least in part on identifying that the one or more positive slopes of the plurality of temperature values are lower than the positive slope for the pregnancy baseline of temperature values for the user; and
generate a message for display on a graphical user interface of the user device that indicates the indication of the early pregnancy loss.

18. The apparatus of claim 17, wherein the instructions are further executable by the processor to cause the apparatus to:
compute a deviation in the time series of the plurality of temperature values relative to the pregnancy baseline of temperature values for the user based at least in part on determining the time series, wherein the deviation comprises a decrease in the plurality of temperature values from the pregnancy baseline of temperature values for the user, wherein identifying that the plurality of temperature values are lower than the pregnancy baseline of temperature values is based at least in part on computing the deviation.

19. The apparatus of claim 17, wherein the physiological data further comprises heart rate data, and wherein the instructions are further executable by the processor to cause the apparatus to:
acquire the heart rate data via one or more light-emitting components and one or more light-receiving components of the wearable ring device; and
determine that the received heart rate data exceeds a pregnancy baseline heart rate for the user for at least a portion of the plurality of days, wherein detecting the indication of the early pregnancy loss is based at least in part on determining that the received heart rate data exceeds the pregnancy baseline heart rate for the user.

20. A non-transitory computer-readable medium storing code, the code comprising instructions executable by a processor to:
acquire, via one or more temperature sensors of a wearable ring device configured to be worn by a user that is pregnant, physiological data associated with the user;
receive, via a transceiver of a user device and from the wearable ring device, the physiological data associated with the user, the physiological data comprising at least temperature data;
determine a time series of a plurality of temperature values taken over a plurality of days based at least in part on the received temperature data;
identify that the plurality of temperature values are lower than a pregnancy baseline of temperature values for the user based at least in part on determining the time series;
identifying that one or more positive slopes of the plurality of temperature values are lower than a positive slope of the pregnancy baseline of temperature values for the user based at least in part on determining the time series;
detect an indication of an early pregnancy loss of the user based at least in part on identifying that the plurality of temperature values are lower than the pregnancy baseline of temperature values for the user and based at least in part on identifying that the one or more positive slopes of the plurality of temperature values are lower than the positive slope for the pregnancy baseline of temperature values for the user; and
generate a message for display on a graphical user interface of the user device that indicates the indication of the early pregnancy loss.

* * * * *